US012631640B2

(12) United States Patent　Tao et al.

(10) Patent No.: US 12,631,640 B2
(45) Date of Patent: May 19, 2026

(54) SYSTEMS AND METHODS FOR IDENTIFYING SUBTYPE, PROGNOSIS, AND MONITORING OF BREAST CANCER

(71) Applicant: Purdue Research Foundation, West Lafayette, IN (US)

(72) Inventors: Weiguo Andy Tao, West Lafayette, IN (US); I-Hsuan Chen, White Plains, NY (US); Hillary Andaluz Aguilar, West Lafayette, IN (US); Juan Sebastian Paez Paez, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 1285 days.

(21) Appl. No.: 17/436,530

(22) PCT Filed: Mar. 3, 2020

(86) PCT No.: PCT/US2020/020843
§ 371 (c)(1),
(2) Date: Sep. 3, 2021

(87) PCT Pub. No.: WO2020/180896
PCT Pub. Date: Sep. 10, 2020

(65) Prior Publication Data
US 2022/0178924 A1　Jun. 9, 2022

Related U.S. Application Data

(60) Provisional application No. 62/813,088, filed on Mar. 3, 2019.

(51) Int. Cl.
*G01N 33/57515* (2026.01)
*G01N 33/50* (2006.01)

(52) U.S. Cl.
CPC ... *G01N 33/57515* (2026.01); *G01N 33/5023* (2013.01); *G01N 2333/4712* (2013.01); *G01N 2333/91205* (2013.01)

(58) Field of Classification Search
CPC ......... G01N 33/57515; G01N 33/5023; G01N 2333/4712; G01N 2333/91205; G01N 2333/912; G01N 2440/10; G01N 2440/14; G01N 33/5308
See application file for complete search history.

(56) References Cited

U.S. PATENT DOCUMENTS

2011/0217297 A1* 9/2011 Kao ........................ A61P 35/00
514/249
2018/0196051 A1 7/2018 Tao et al.

FOREIGN PATENT DOCUMENTS

| CN | 109060989 | 12/2018 |
| WO | WO-2017149206 A1 * | 9/2017 |
| WO | 2018098379 A1 | 5/2018 |
| WO | 2019033041 A1 | 2/2019 |

OTHER PUBLICATIONS

Eifert, Cheryl et al. "A novel isoform of the B cell tyrosine kinase BTK protects breast cancer cells from apoptosis." Genes, chromosomes & cancer vol. 52,10 (2013): 961-75. doi:10.1002/gcc.22091 (Year: 2013).*
Ignatov, Tanja et al. "Management of small T1a/b breast cancer by tumor subtype." Breast cancer research and treatment vol. 163,1 (2017): 111-118. doi: 10.1007/s10549-017-4168-x (Year: 2017).*
International Searching Authority, International Search Report, PCT Application No. PCT/US2020/020843, dated Jul. 21, 2020, US.
International Searching Authority, Written Opinion of the International Searching Authority, PCT Application No. PCT/US2020/020843, dated Jul. 21, 2020, US.

* cited by examiner

*Primary Examiner* — Gregory S Emch
*Assistant Examiner* — Mckenzie A Dunn
(74) *Attorney, Agent, or Firm* — Reichel Stohry Dean LLP; Natalie J. Dean

(57) ABSTRACT

Noninvasive methods of determining breast cancer subtype in a subject are provided that employ newly identified biomarkers. Said methods comprise isolating a population of extracellular vehicles in a biofluid sample of a subject and detecting differential expression in one or more proteins or peptides therein. Such differential expression is compared to one or more expression profiles within a panel of biomarkers, with each expression profile in the panel associated with a subtype of breast cancer. Also provided are kits for detecting a subtype of breast cancer and/or identifying the recurrence thereof, each comprising an antibody, aptamer, or other detection means against the aforesaid biomarkers. Methods for monitoring treatment efficacy in a subject experiencing breast cancer using the same platforms are also provided.

10 Claims, 20 Drawing Sheets

300

ID: 914 acetylated (K) peptides/331 proteins
187 quantified acetylated proteins
373 quantified acetylated (K) sites ID: 1035 glycopeptides/504 glycoproteins
matched motif (N-X-S/T)
481 quantified glycoproteins
1078 quantified glycosites

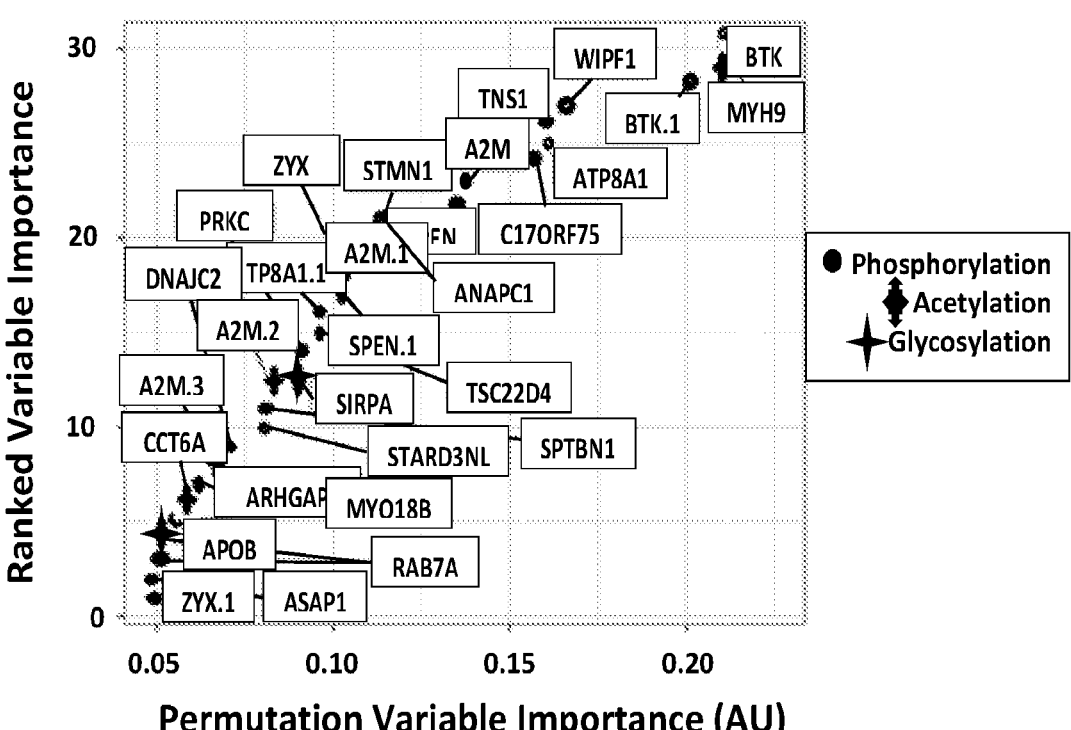
Figure 9A
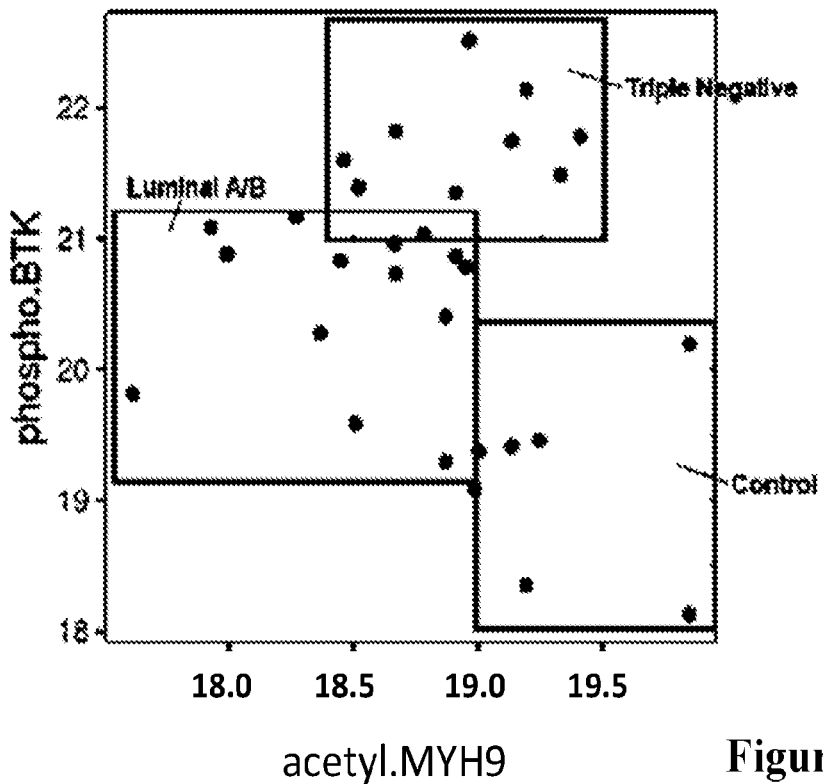
acetyl.MYH9        Figure 9B

SYSTEMS AND METHODS FOR IDENTIFYING SUBTYPE, PROGNOSIS, AND MONITORING OF BREAST CANCER

PRIORITY

This application is related to and claims priority benefit of, and is a 35 U.S.C. 371 national stage application of International Patent Application No. PCT/US2020/020843, filed Mar. 3, 2020, which is related to and claims the priority benefit of U.S. Provisional Patent Application Ser. No. 62/813,088 to Tao et al. filed Mar. 3, 2019. This application is further related, but does not claim priority, to U.S. patent application Ser. No. 15/864,376 to Tao et al. filed Jan. 8, 2018, which is related to and claims the priority benefit of U.S. Provisional Application Ser. No. 62/443,400, filed Jan. 6, 2017. The contents of the aforementioned applications are hereby incorporated by reference in their entireties into this disclosure.

STATEMENT OF GOVERNMENT SUPPORT

This invention was made with government support under GM111788 awarded by the National Institute of Health. The government has certain rights in the invention.

BACKGROUND

Cancer is the leading cause of disease worldwide, with breast cancer being one of the most common forms affecting both females and males globally. For example, in 2020 in the United States alone, an estimate of 276,480 new cases of invasive breast cancer are expected to be diagnosed in women and 2,620 new cases of invasive breast cancer in men. Breast cancer is diagnosed every 29 seconds around the world and every 2 minutes in the United States. For women in the United States, breast cancer death rates are second only to those associated with lung cancer.

Breast cancer is a heterogeneous complex of diseases that includes a spectrum of many molecular subtypes with distinct biological features, including the histopathological type of tumor, the grade of the tumor, the stage of the tumor, and the expression of genes which are characteristic of particular subtypes of breast cancer, to name a few. These different molecular subtypes are associated with distinct clinical outcomes (see FIGS. 1A and 1B).

There are three major molecular subtypes with breast cancer: luminal A/B, HER2, and triple negative. Luminal A/B tumor cells look the most like cells of breast cancers that start in the inner (luminal) cells lining the mammary ducts. Luminal A/B tumors tend to be estrogen receptor-positive (ER+) and progesterone receptor-positive (PR+), with luminal A tumors being HER2 receptor-negative (HER2−) and luminal B tumors being HER2 receptor-positive (HER2+). ER+ tumor receptors, which are present on the cellular surface, can be targeted with endocrine therapies (and trastuzumab or the like in the case of HER2+/luminal B). Accordingly, patients with the luminal A/B subtype commonly receive adjuvant endocrine therapy (in tandem with traditional chemotherapy), which serves to inhibit estrogen receptor-signaling, which has been found to drive ER+ breast cancer.

Despite having the best clinical outcome and survival rate of all of the subtypes, most deaths from metastatic breast cancer come from patients with the luminal A/B subtype. Although endocrine therapy reduces the risk of disease recurrence and breast cancer-related mortality, a third of the patients with ER+ breast cancer experience primary or acquired endocrine resistance and experience disease relapse.

In about 20% of breast cancers, the cancer cells have a gene mutation that makes an excess of a protein called human epidermal growth factor receptor 2 (HER2), which promotes the growth of the cancer cells. HER2+ breast cancers tend to be more aggressive and fast-growing than other types of breast cancer and are less sensitive to hormone therapy; however, treatments such as trastuzumab, neratinib, pertuzumab, and the like that specifically target HER2 typically have a high degree of efficacy.

In the triple negative breast cancer (TNBC) subtype, tumors are estrogen receptor-negative (ER−), progesterone receptor-negative (PR−), and HER2-negative (HER2−), indicating that tumor growth is not fueled by the hormones estrogen and progesterone, or by the HER2 protein. Accordingly, TNBC is unlikely to respond to endocrine or other hormonal therapies (such as tamoxifen and aromatase inhibitors) or medicines that target HER2 protein receptors (such as trastuzumab, neratinib, pertuzumab, or lapatinib).

TNBC represents about 15-20% of all newly diagnosed breast cancers and most BRCA1-related cancers are TNBC. TNBC tumors are often aggressive and have a poorer prognosis as compared to the ER+ subtypes, demonstrating higher relapse and death rates in part due to limited therapeutic options. Instead of the hormonal or HER2 protein receptor targeted therapies used with other subtypes, TNBC is typically treated with neoadjuvant chemotherapy, PARP inhibitors (such as olaparib and talazoparib) and immunotherapies. However, because it often takes a significant amount of time to accurately determine subtype using conventional methods, many TNBC will first receive ineffective endocrine therapy (the first-line therapy for receptor-positive patients). This is a major contributing factor to the survival rate of TNBC being 3 to 5 years.

Accordingly, determining the particular subtype of cancer in a patient as early as possible following diagnosis is often of critical importance because the subtypes exhibit different response patterns to various treatment modalities. As noted above, treatment and disease progression is typically much different between the subtypes, with certain subtypes being clinically nonresponsive to treatments that are effective for others. Accordingly, the ability to quickly and accurately identify the particular molecular subtype of breast cancer in a patient is of paramount importance and can greatly influence treatment decisions and, ultimately, clinical outcomes.

Despite this, traditional classification systems that assess biological features of tumors have many limitations. The existence of breast cancer and/or a tumor is usually first indicated with imaging modalities or through manual palpation. These screening strategies are lacking in sensitivity as the tumors must grow large enough that they can be seen on a mammogram, MRI or the like, and/or felt in a manual breast exam before they are detected.

Currently, a tissue biopsy is the only definitive way to make a diagnosis of breast cancer. Where initial screening procedures (such as imaging modalities and/or breast exams) indicating follow up is warranted, a specialized needle device guided by X-ray or other imaging means are used to extract a core of tissue from the suspicious area, which is then sent to a laboratory for analysis to determine if the cells are cancerous. The biopsy sample may also then be analyzed to determine the types of cells involved, the aggressiveness (grade) of the cancer, and to analyze the presence or absence of molecular receptors to determine subtype.

As biopsies and the subsequent cellular analysis is not performed until after the tumor is large enough to either manually palpate or to show up in a mammogram, ultrasound, or MRI, conventional options cannot provide for detection prior to disease onset. Furthermore, biopsy tissue from tumors is not available for monitoring patient response over the course of treatment.

After curative primary treatment, approximately 15% of breast cancer survivors will develop a second breast malignancy within ten years, with most recurrences happening in the first five years after primary breast cancer treatment. Breast cancer can come back as a local recurrence (i.e. in the treated breast or near the mastectomy scar) or somewhere else in the body (regional, distant, or metastatic recurrence), with the most common cites of distant recurrence being the lymph nodes, bones, liver, lungs, and brain. Further, reoccurrence rates in these cancers are increasing due to primary or acquired resistance, or lack of pharmacological treatment resulting in a higher rate of therapeutic or prophylactic mastectomies. Importantly, breast cancer subtype can change from the primary tumor to the recurrence, with discordance between the two having implications for further treatment options and the ultimate prognosis.

Accordingly, there is a need for improved methods for the diagnosis of specific subtypes of breast cancer to help guide treatment plans. There is also a need for methods of prognosis, and for the early detection of responsiveness to treatment, in patients diagnosed with breast cancer and undergoing treatment.

BRIEF SUMMARY

Novel methods of determining breast cancer subtype in a subject are provided. In at least one embodiment, such methods comprise obtaining (or having obtained) an amount of a sample taken from a subject; isolating a population of extracellular vehicles (EVs) in the sample and identifying differential expression of one or more proteins or peptides in the isolated EVs as compared to an expression level of such EV proteins or EV peptides in a control; and, comparing the differential expression in the isolated EVs to one or more expression profiles within a panel of biomarkers. The sample may comprise blood, plasma, urine, serum or any other biofluid sample and, as such, the method is noninvasive and simple to use as compared to conventional biopsy and imaging techniques. In at least one exemplary embodiment, the subject may comprise a human.

As each expression profile in the panel is associated with a subtype of breast cancer, a diagnosis of the subject can be made where the isolated EVs positively correlate with one of the expression profiles. A first expression profile, for example, may be associated with a first subtype comprising luminal A/B breast cancer (LAB), a second expression profile may be associated with a second subtype comprising triple negative breast cancer (TNBC), and a third expression profile may be associated with a third subtype comprising HER2. Still further, a first expression profile of the panel of biomarkers may comprise overexpression of phosphorylated bruton tyrosine kinase (BTK) and equivalent expression of acetylated myosin heavy chain 9 (MYH9), both as compared to a control, with a match or positive correlation to the first expression profile being associated with the sample donor experiencing the TNBC subtype. Additionally, the method may further comprise a second expression profile of the panel of biomarkers comprising overexpression of BTK and underexpression of MYH9, both as compared to a control, with a positive correlation or match to the second expression profile being associated with the sample donor experiencing the LAB subtype. Accordingly, the method may further comprise diagnosing the subject with the subtype of breast cancer associated with the at least one expression profile with which the differential expression in the isolated EVs positively correlates.

The results of such methods may ultimately drive treatment decisions. As such, in at least one exemplary embodiment, the method further comprises administering or having administered endocrine therapy to the subject when a positive correlation or match is identified with the one or more expression profiles of the panel of biomarkers comprising overexpression of BTK and underexpression of MYH9, both as compared to a control, which is indicative of the LAB subtype. Alternatively, such administering step may comprise administering or having administered a therapeutically effective dose of trastuzumab to the subject where, for example, a positive correlation or match is identified between the sample EV-expression and one or more expression profiles associated with the HER2 subtype. Still further, the method may comprise administering or having administered one or more of neoadjuvant chemotherapy, PARP inhibitors, and immunotherapy to the subject where, for example, a positive correlation or match is identified with the one or more expression profiles of the panel of biomarkers comprising overexpression of BTK and equivalent expression of MYH9, both as compared to a control, which is indicative subtype TNBC.

In at least one exemplary embodiment, the panel of biomarkers may comprise one or more of the proteins or genes listed in Table 3 below, or a peptide or fragment thereof.

Still further, the step of identifying differential expression may comprise quantifying a level of expression of one or more proteins or peptides in the isolated EVs using methodologies described herein or otherwise known in the art. For example, and without limitation, the step of identifying may be performed using mass spectrometry, a peptide assay, an enzyme linked immunosorbent assay (ELISA), an antibody against each of the one or more proteins or peptides, or an aptamer against each of the one or more proteins or peptides.

In certain embodiments of the methods hereof, the comparing step may further comprise performing parallel reaction monitoring or multi-reaction monitoring between the isolated EVs and the panel of biomarkers, and scoring a degree of correlation between the same. Additionally or alternatively, the expression levels of the EV-isolated proteins or peptides may simply be compared to those of the various expression profiles to determine if there is a match and, if so, how close of a match exists.

Novel kits for determining a subtype of breast cancer in a subject are also provided. In at least one exemplary embodiment, such a kit comprises a means to detect and quantify a panel of EV-biomarkers isolated from a biofluid sample, wherein the biomarkers of the panel are selected from a group consisting of phosphoproteins, glycoproteins, acetylated proteins, methylated proteins, and ubiquitinated proteins. In at least one exemplary embodiment, the panel of biomarkers comprises one or more of the markers listed in Table 3 or peptides or fragments thereof. The kit may comprise a receptacle for receiving/holding the biofluid sample and/or any other tools that may be useful in collecting such biofluid sample from the subject (e.g., a tunicate, etc.).

The means to detect and quantify of the kit may comprise one or more antibodies made against one or more of the biomarkers of the panel. Additionally or alternatively, the means to detect and quantify may comprise one or more aptamers made against one or more of the biomarkers of the panel. Still further, the means to detect or quantify may comprise any other methodology useful therefore as described herein or the reported protocol (as defined herein).

In at least one embodiment, a first expression profile of the panel of biomarkers may comprise overexpression of phosphorylated BTK and equivalent expression of acetylated MYH9, both as compared to a control, with the first expression profile associated with the TNBC subtype, and/or a second expression profile of the panel of biomarkers comprising overexpression of BTK and underexpression of MYH9, both as compared to a control, with the second expression profile associated with the LAB subtype.

Methods of monitoring treatment efficacy in a subject experiencing or having experienced breast cancer are also provided. There, in at least one exemplary embodiment, the method comprises: obtaining or having obtained an amount of a sample taken from a subject who has received a first treatment for breast cancer (such as, for example and without limitation, a chemotherapy, an endocrine therapy, and/or a mastectomy); isolating a population of EVs in the sample; identifying a differential expression of one or more proteins or peptides in the isolated EVs as compared to an expression level of such EV proteins or EV peptides in a control; comparing the differential expression in the isolated EVs to one or more expression profiles within a panel of biomarkers, wherein each expression profile in the panel is associated with a subtype of breast cancer; and using the panel of biomarkers to evaluate a therapeutic effect of the first treatment on the subject. Importantly, the sample may be a biofluid comprising, for example, plasma derived from peripheral blood, urine, plasma, serum and/or any other biofluid containing EVs. In at least one exemplary embodiment, the subject is a human. Furthermore, the panel of biomarkers may comprise at the least the markers listed in Table 3, or fragments or peptides thereof, including, without limitation, acetylated MYH9 and phosphorylated BTK.

Where the first treatment is deemed ineffective (or less effective than desired) and/or a result of the panel evaluation is indicative of the subject experiencing a recurrent breast cancer, the method may optionally comprise administering or having administered a second treatment. In at least one embodiment, the method may additionally comprise using the panel of biomarkers to identify a subtype of the recurrent breast cancer in the subject by diagnosing the subject with the subtype of breast cancer associated with the at least one expression profile of the panel with which the differential expression in the isolated EVs positively correlates or otherwise matches.

BRIEF DESCRIPTION OF THE DRAWINGS

The disclosed embodiments and other features, advantages, and aspects contained herein, and the matter of attaining them, will become apparent in light of the following detailed description of various exemplary embodiments of the present disclosure. Such detailed description will be better understood when taken in conjunction with the accompanying drawings, wherein:

FIG. 9A shows a variable importance ranking of the top 30 targets identified with respect to distinguishing between breast cancer subtypes (Luminal A/B group and TNBC group) and the control (Healthy Control group);

FIG. 9B shows a scatterplot depicting log-2 intensities of the top two proteins identified (phosphor.BTK and acetyl.MYH9) to distinguish between breast cancer subtypes and the control groups, with the x- and y-axis defined by values set pursuant to the scoring model;

Figure 1A:
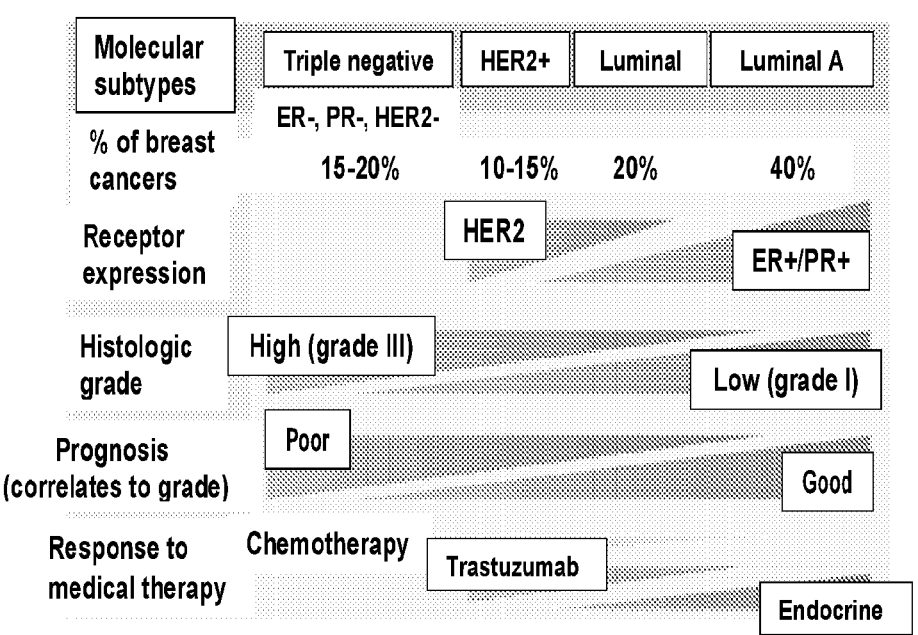
FIGS. 1A and 1B show graphical representations of the different molecular subtypes of breast cancer and their associated distinct clinical outcomes, with FIG. 1A illustrating that triple negative tumors respond best to chemotherapy (similar to other aggressive cancers) and luminal A tumors response best to endocrine therapy (e.g., antiestrogen or aromatase inhibitors)
Figure 1B:
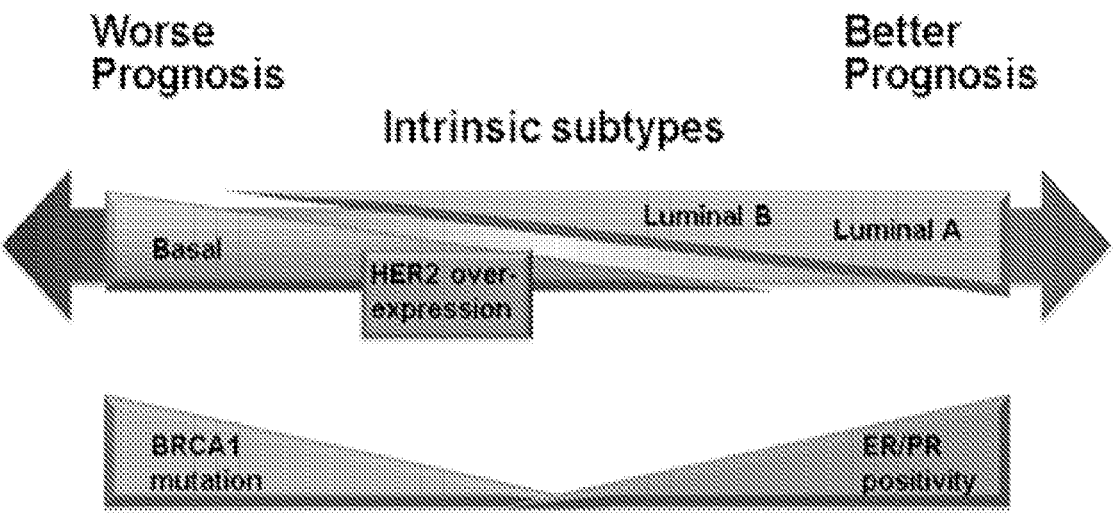

While the present disclosure is susceptible to various modifications and alternative forms, exemplary embodiments thereof are shown by way of example in the drawings and are herein described in detail.

DETAILED DESCRIPTION

For the purposes of promoting an understanding of the principles of the present disclosure, reference will now be made to the embodiments illustrated in the drawings and specific language will be used to describe the same. It will nevertheless be understood that no limitation of scope is intended by the description of these embodiments. On the contrary, this disclosure is intended to cover alternatives, modifications, and equivalents as may be included within the spirit and scope of this application as defined by the appended claims. As previously noted, while this technology may be illustrated and described in one or more preferred embodiments, the compositions, systems and methods hereof may comprise many different configurations, forms, materials, and accessories.

In the following description, numerous specific details are set forth in order to provide a thorough understanding of the present disclosure. Particular examples may be implemented without some or all of these specific details and it is to be understood that this disclosure is not limited to particular biological systems, which can, of course, vary.

Unless defined otherwise, all technical and scientific terms used herein have the same meaning as commonly understood by one of skill in the relevant arts. Although any methods and materials similar to or equivalent to those described herein can be used in the practice or testing of the subject of the present application, the preferred methods and materials are described herein. Additionally, as used in this specification and the appended claims, the singular forms "a", "an" and "the" include plural referents unless the content clearly dictates otherwise. Furthermore, unless specifically stated otherwise, the term "about" refers to a range of values plus or minus 10% for percentages and plus or minus 1.0 unit for unit values, for example, about 1.0 refers to a range of values from 0.9 to 1.1.

The terms "post-translational modifications" and "PTMs" mean chemical modifications of the proteome that occur on one or more protein residues and provide functional heterogeneity to an existing proteome. PTMs may include, without limitation, phosphorylation, glycosylation, acetylation, methylation, propionylation, butyrylation, crotonylation, succinylation, malonylation, glutarylation, and the like.

The term "phosphoprotein" refers to a protein that has been post-translationally modified such that a phosphate group, or a complex molecule such as 5'-phospho-DNA, has been transferred to an amino acid residue of the protein. The phosphate group can be transferred by enzymatic action within a cell to any amino acid including, but not limited to, serine, threonine, and tyrosine residues (mostly in eukaryotes) or aspartic acid and histidine residues (mostly in prokaryotes).

The term "glycoprotein" refers to a protein that has been post-translationally modified such that a carbohydrate, carbohydrate chain or sugar moiety (i.e. a glycosyl donor) is attached to an amino acid residue of the protein. The carbohydrate may affect the three-dimensional configuration of the resulting glycoprotein. Glycosylation (the reaction resulting in a glycoprotein) often provides greater proteomic diversity than other post-translational modifications and is characterized by various glycosidic linkages, including N-, O- and C-linked glycosylation, glypiation, and phosphoglycosylation.

The term "acetylation" refers to the transfer of an acetyl group ($CH_3CO$) onto a small molecule, metabolite, or protein. The acetyl group can react with a variety of atoms or functional groups on a target molecule/protein and, while acetylation can occur with thiol groups (sulfur), hydroxyl groups (oxygen), amino groups (nitrogen), and lysine, serine, threonine, and histidine residues of proteins, in the present disclosure, the majority of acetylation is on the lysine residues in proteins.

The terms "acetylated protein" and "acetylated residue" refers to a protein or portion thereof that has been post-translationally modified such that an acetyl functional group is attached to an amino acid residue of the protein.

As used herein, the terms "detecting," "detected," and "detection" refer to confirming the presence of a detectable moiety by observing the occurrence of a detectable signal, such as a radiologic, colorimetric, fluoroscopic, chemiluminescent, or spectroscopic signal that will appear exclusively in the presence of the detectable moiety.

A "subject" or "patient" as the terms are used herein is a mammal. While preferably a human, the terms can also refer to a non-human mammal, such as a mouse, cat, dog, monkey, horse, cattle, goat, or sheep, and is inclusive of male, female, adults, and children.

The terms "treatment" or "therapy," as used herein include curative and/or prophylactic treatment. More particularly, curative treatment refers to any of the alleviation, amelioration and/or elimination, reduction and/or stabilization (e.g., failure to progress to more advanced stages) of a symptom, as well as delay in progression of a symptom of a particular disorder. Prophylactic treatment refers to any of the following: halting the onset, reducing the risk of development, reducing the incidence, delaying the onset, reducing the development, and increasing the time to onset of symptoms of a particular disorder.

As used herein, the term "therapeutically effective dose" means (unless specifically stated otherwise) a quantity of a compound which, when administered either one time or over the course of a treatment cycle affects the health, wellbeing or mortality of a subject (e.g., and without limitation, delays the onset of and/or reduces the severity of one or more of the symptoms associated with an active infection or cervical cancer). The amount of the compound to be administered to a recipient will depend on the type of disease being treated, how advanced the disease pathology is, and the characteristics of the patient or subject (such as general health, age, sex, body weight, and tolerance to drugs).

The term "pharmaceutically acceptable" and grammatical variations thereof, as they refer to compositions, carriers, diluents, and reagents, are used interchangeably and represent that the materials are capable of administration to or upon a mammal without the production of undesirable physiological effects such as nausea, dizziness, gastric upset, and the like.

"Down-regulation" or "down-regulated" may be used interchangeably and refer to a decrease in the level of a marker, such as a gene, nucleic acid, metabolite, transcript, protein, or polypeptide, as compared to an established level (e.g., that of a healthy cohort or the subject of interest). "Up-regulation" or "up-regulated" may also be used interchangeably and refer to an increase in the level of a marker, such as a gene, nucleic acid, metabolite, transcript, protein, or polypeptide, as compared to an established level (e.g., that of a healthy control or the subject of interest).

A "marker" or "biomarker" as the terms are used herein may be described as being differentially expressed when the level of expression in a subject who is experiencing an active disease state is significantly different from that of a subject or sample taken from a healthy subject. A differentially expressed marker may be overexpressed or underexpressed as compared to the expression level of a normal or control sample or subjects' baseline (i.e. down-regulated). The increase or decrease, or quantification of the markers in a biological sample may be determined by any of the several methods known in the art for measuring the presence and/or relative abundance of a gene product or transcript. The level of markers may be determined as an absolute value, or relative to a baseline value, and the level of the subject's markers compared to a cutoff index. Alternatively, the relative abundance of the marker or markers may be determined relative to a control, which may be a clinically normal subject.

A "profile" or "assay" or "panel" is a set of one or more markers and their presence, absence, and/or relative level or abundance (relative to one or more controls). For example, a panel of PTMs is a dataset of the presence, absence, relative level or abundance of the PTMs or target proteins of interest present within a sample. A genomic or nucleic acid profile is a dataset of the presence, absence, relative level or abundance of expressed nucleic acids (e.g., transcripts, mRNA, or the like). A profile may alternatively be referred to as an expression profile or expression pattern.

As used herein the terms "detection limit," "limit of detection," or "LOD" means the lowest concentration or quantity of a substance that can be reliably measured by an analytical procedure.

As used herein, the term "point of care" or "POC" means the point in time when clinicians or other healthcare providers delivery healthcare products and services to patients at the time of care. Diagnostic testing that occurs at POC is performed at or near the point of care/bedside (as compared to historical testing which was wholly or mostly confined to the medical laboratory—i.e. sending specimens away).

The term "isolated" means that the material is removed from its original environment, e.g., the natural environment if it is naturally occurring. For example, a naturally-occurring polypeptide present within a living organism is not isolated, but the same polypeptide separated from some or all of the coexisting materials in the natural system is isolated.

The term "purified" does not require absolute purity; instead, it is intended as a relative definition.

The present disclosure provides novel systems and methods for using a novel liquid biopsy platform to accurately and noninvasively identify the specific subtype of breast cancer in a patient by assessing proteins extracted from plasma-derived extracellular vesicles (EVs). As described herein in additional detail below, these EVs carry a wealth of biological information from the host cells. Where the host cell is a tumor cell, analyzing proteins with post-translational modifications (PTMs) from an EV's cargo can provide a read of cellular regulation and processes associated with signaling pathways that reflect tumor biology, thus opening a window to the physiology of the tumor. Systems and methods hereof may further be adapted to closely monitor the progression of breast cancer, to precisely monitor the response to cancer treatment, and/or to monitor for recurrence onset such that it can be detected as early as possible.

Early diagnosis and monitoring of diseases such as cancers through blood tests has been a decades-long aim of medical diagnostics. Because protein phosphorylation is one of the most important and widespread molecular regulatory mechanisms that controls almost all aspects of cellular functions, the status of phosphorylation events conceivably provides clues regarding disease status. However, few phosphoproteins have been developed as disease markers to date. Assays of phosphoproteins from tissues face tremendous challenges because of the invasive nature of the tissue biopsy and the highly dynamic nature of protein phosphorylation during the typically long and complex procedure of a tissue biopsy. Furthermore, using phosphoproteins as disease markers from biofluids has conventionally been even more challenging because blood tends to have high concentrations of active phosphatases and, as such, few phosphorylated proteins in plasma/serum can be identified with stable and detectable concentrations using conventional techniques.

Figure 2:
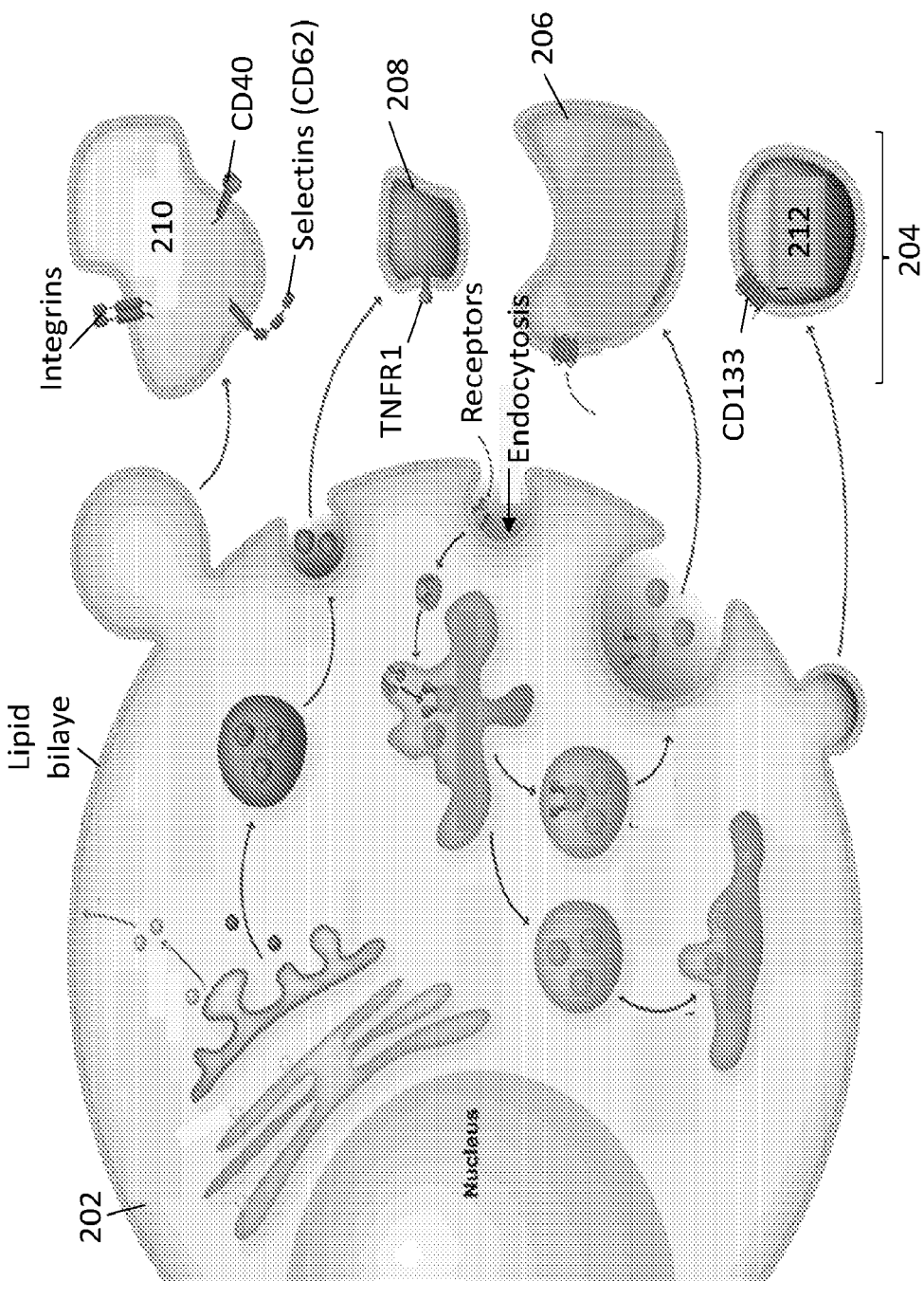
FIG. 2 is a schematic representation of a eukaryotic cell and the synthesis of extracellular vesicles (EVs) therefrom, as well as illustrations of the various different types of EVs.

EVs are emerging as important biological carriers for intercellular communications and are produced by all domains of life including complex eukaryotes, both Gram-negative and Gram-positive bacteria, mycobacteria, and fungi. Generally, and as illustrated in FIG. 2, EVs 204 are membrane-encapsulated nano- or microparticles that are naturally released from a cell 202 and, unlike a cell, cannot replicate. EVs 204 carry a cargo of proteins, nucleic acids, lipids, metabolites, and even organelles from the parent cell 202, with such cargo being protected from external proteases, phosphatases, and other enzymes by the outer membrane of the EV. Accordingly, EVs are highly stable in biofluid for extended periods of time.

There are many types of EVs 204 ranging in diameter from around 20-30 nm to as large as 10 microns or more, although the vast majority of EVs 204 have a diameter of less than about 200 nm. A wide variety of EV subtypes have been proposed, defined variously by size, biogenesis pathway, cargo, cellular source, and function. For example, exosomes 206 are membrane bound extracellular vesicles of endocytic origin (about 30-150 nm in diameter) enriched in CD63 and CD81. Exosomes 206 (including exosome-like vesicles 208) have been isolated and characterized from different biological fluids such as urine, BAL fluid, and serum. Microvesicles 210 (also referred to as shedding microvesicles (SMVs)) are shed directly from the plasma membrane and are typically between about 20-100 nm in diameter. Membrane particles 212 (about 50-80 nm in diameter), or large membranous vesicles (about 600 nm in diameter) include CD133$^+$ and CD63$^+$. Apoptotic blebs/bodies or vesicles (not shown) (about 1000-5000 nm in diameter) are released by dying cells undergoing apoptosis. Since apoptotic cells tend to display phosphatidylserine (PS)

in the outer bilayer of the cell membrane, apoptotic bodies tend to externalize PS and tend to be quite large (e.g., microns in diameter).

EVs' 204 cargo (including, for example, proteins, nucleic acids, lipids, metabolites, and even organelle from the parent cell, reflects the molecular signature of the parent cell 202. Considering EVs in the context of tumor biology and cancer, there is strong evidence that EV-based disease markers can be identified well before the onset of symptoms or physiological detection of a tumor, making EVs 204 prime candidates for early cancer detection biomarkers ahead of conventional nuclear imaging studies. Additionally, EVs have been found to circulate through many different biological fluids, including blood and urine as previously noted. Due to the resemblance of EVs composition with the parental cell, circulating EVs have raised considerable interest as a source for the discovery of biomarkers.

Indeed, EV analysis in blood and urine represents a means of reducing the complex composition of body fluids by several orders of magnitude. Thus, the isolation of EVs may result in a large enrichment of low-abundant molecules that may have particular pathophysiological significance. There is growing evidence that EVs reflect the molecule signature of the parent cell. The increase in the understanding of the role of EVs in tumor biology, metastasis and cell signaling has been critical for their establishment as biomarkers for human diseases.

PTMs, including phosphorylation, acetylation, and glycosylation for example, have been used to profile diseases as they are involved in signaling events and multiple, important cellular processes—e.g., signaling transduction, protein degradation, and transcriptional regulation. PTMs represent their own level of biological regulation of the cellular proteome and therefore present a valuable avenue through which human and cellular physiology may be studied ("PTM-omics"). For example, protein phosphorylation is one of the most important and widespread molecular regulatory mechanisms that controls almost all aspects of cellular functions. The status of a phosphorylation event conceivably provides clues regarding disease states. Indeed, abnormal protein phosphorylation has been implicated in a number of diseases including Alzheimer's disease, Parkinson's disease, and other degenerative disorders. In other words, PTMs provide the ability to detect genome output to provide real-time information about a subject's physiological functions, disease progression and, with breast cancer, even breast cancer subtype.

Since EVs are membrane covered nanoparticles whose content is protected from external proteases, enzymes and phosphatases, they are promising candidates for biomarker discovery as well. Additionally, due to large dynamic ranges and the presence of phosphatases and enzymes in the blood, EV content is very valuable for diagnostics/prognostics of diseases like cancer. However, very limited data has been conventionally available on sequential enrichment of these PTMs in EVs, at least in part because of the limited amounts of purified EVs, low-abundance of PTM proteins, and interference from proteins and metabolites in biofluids.

Recently, the present investigators developed an approach to isolate phosphoproteins and glycoproteins in EVs in small volumes of human plasma, which allowed for the identification of nearly 10,000 unique phosphopeptides (PNAS) and 1,500 unique N-glycopeptides (Analytical Chemistry). The approach demonstrated the feasibility of using this data to identify potential markers to differentiate disease from healthy states. Moreover, the present investigators have since developed methods to integrate both enrichments into a single step, thus isolating phosphoproteins and glycoproteins from the same biological sample. see, e.g., Aguilar et al., "Sequential Phosphoproteomics and N-glycoproteomis of Plasma-Derived Extracellular Vesicles," Nat Protoc, 2020 January; 15(1): 161-180 (as used herein, the "reported protocol"), the entire contents of which is incorporated by reference into the present disclosure.

As supported by the data presented herein, the combination of different PTMs (e.g., and without limitation, phosphoproteins, glycoproteins, acetylated proteins, methylated proteins, ubiquitinated proteins, and/or other modified proteins) isolated from plasma EV in breast cancer subjects allows for the delineation of breast cancer subtypes. Furthermore, by identifying particular PTMs expression profiles associated with specific breast cancer subtypes and validating such data in clinical studies, novel EV-based biomarkers have been identified that facilitate breast cancer subtype diagnosis which, in at least one embodiment, may be performed at POC.

Due to its high sensitivity and high-throughput, tandem mass spectrometry has been the leading tool to date in studying PTMs on a global proteome level. For example, one can profile the global lysine acetylome of an organism, identifying acetyllysine sites within a given proteome.

In addition to using these EV-based disease markers to diagnose the presence of breast cancer, the present disclosure establishes that certain PTM biomarkers can also be utilized to distinguish between breast cancer subtypes (even at the early stages of breast cancer) to allow for patients to receive the most effective therapies as soon as possible. This advancement has the potential to universally increase the survival rate of breast cancer patients as it provides a viable, cost-efficient, and noninvasive mechanism for early detection and subtyping so effective treatment can be initiated as soon as possible. Moreover, the methods hereof also allow for the evaluation of plasma EVs in patients that undergo mastectomy procedures; heretofore their diagnostic/surveillance options were limited as they lack breast tissue for biopsies and the like. Still further, the systems and methods of the present disclosure allow for near-real-time monitoring of post-curative treatment disease recurrence, as well as near-real-time monitoring of treatment efficacy.

Sequential Isolation and Profiling of Plasma-Derived EV Proteome and PTMs 20,788, 11,181, 1,035, and 914 unique peptides, phosphopeptides, glycopeptides, and acetylated peptides, respectively, were identified in plasma-derived EVs that are indicative of, and capable of distinguishing between, particular subtypes of breast cancer.

Figure 3A:
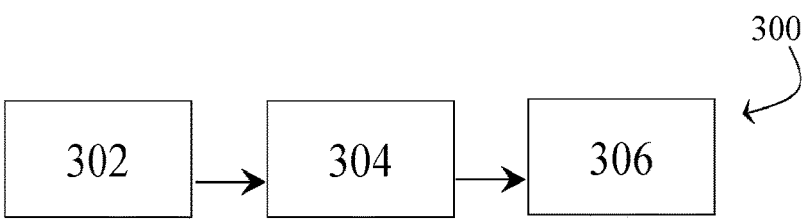
FIG. 3A shows a graphical representation of the overall strategy of the study performed by the present investigators, namely: 1) identify relevant/candidate targets in an unbiased discovery phase; 2) targeted verification of such candidate targets through targeted proteomics and clinical validation by running individual samples from patients to see which of the candidate proteins were present.
Figure 3B:
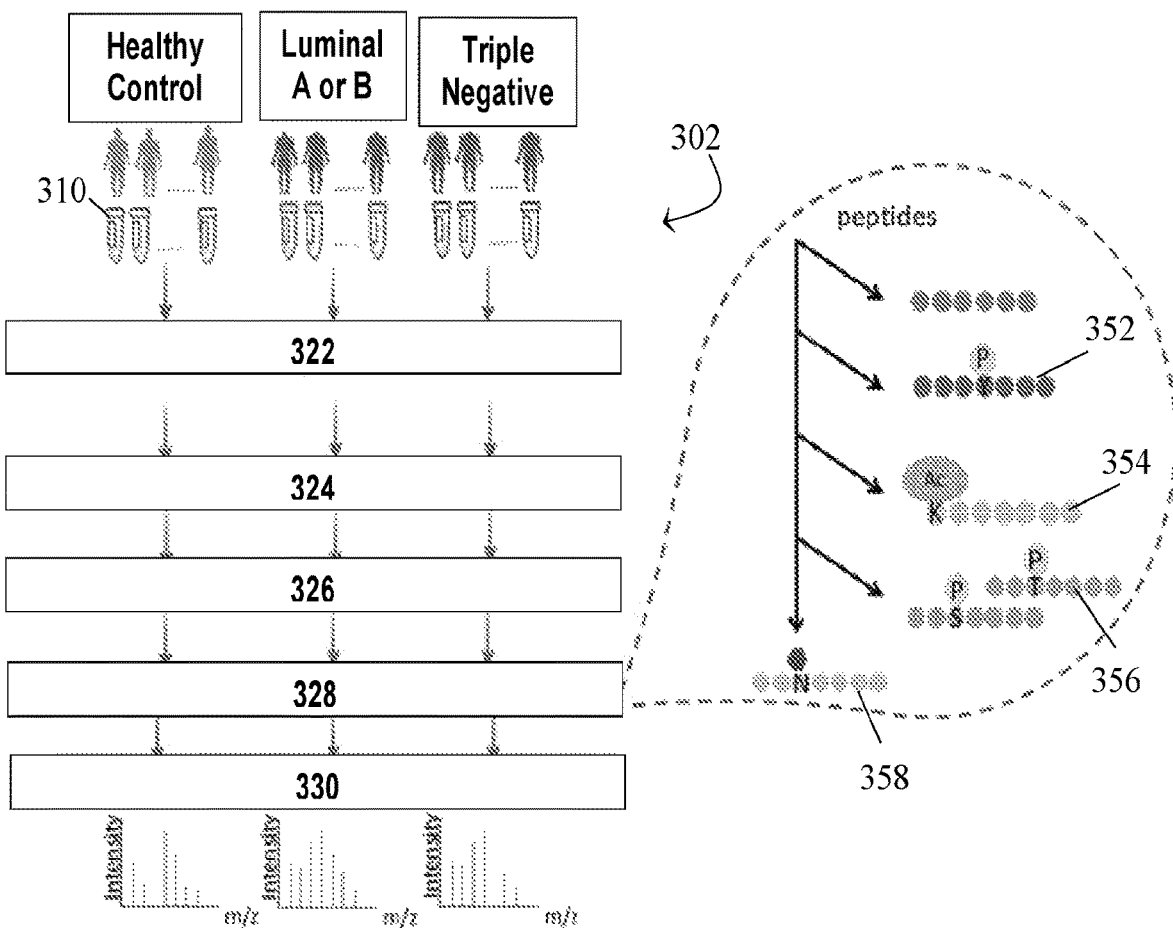
FIG. 3B shows a workflow for revealing breast cancer extracellular vesicles' post-translational modification cargo where plasma samples were pooled from healthy female individuals (n=20) (the "Healthy Control" group), breast cancer patients diagnosed with luminal A or B subtype (n=20) (the "Luminal A/B" group), and breast cancer patients diagnosed with triple negative breast cancer subtype (n=20) (the "TNBC" group) comprising 20 samples of blood obtained from breast cancer patients diagnosed with the TNBC subtype.
Figure 4A:
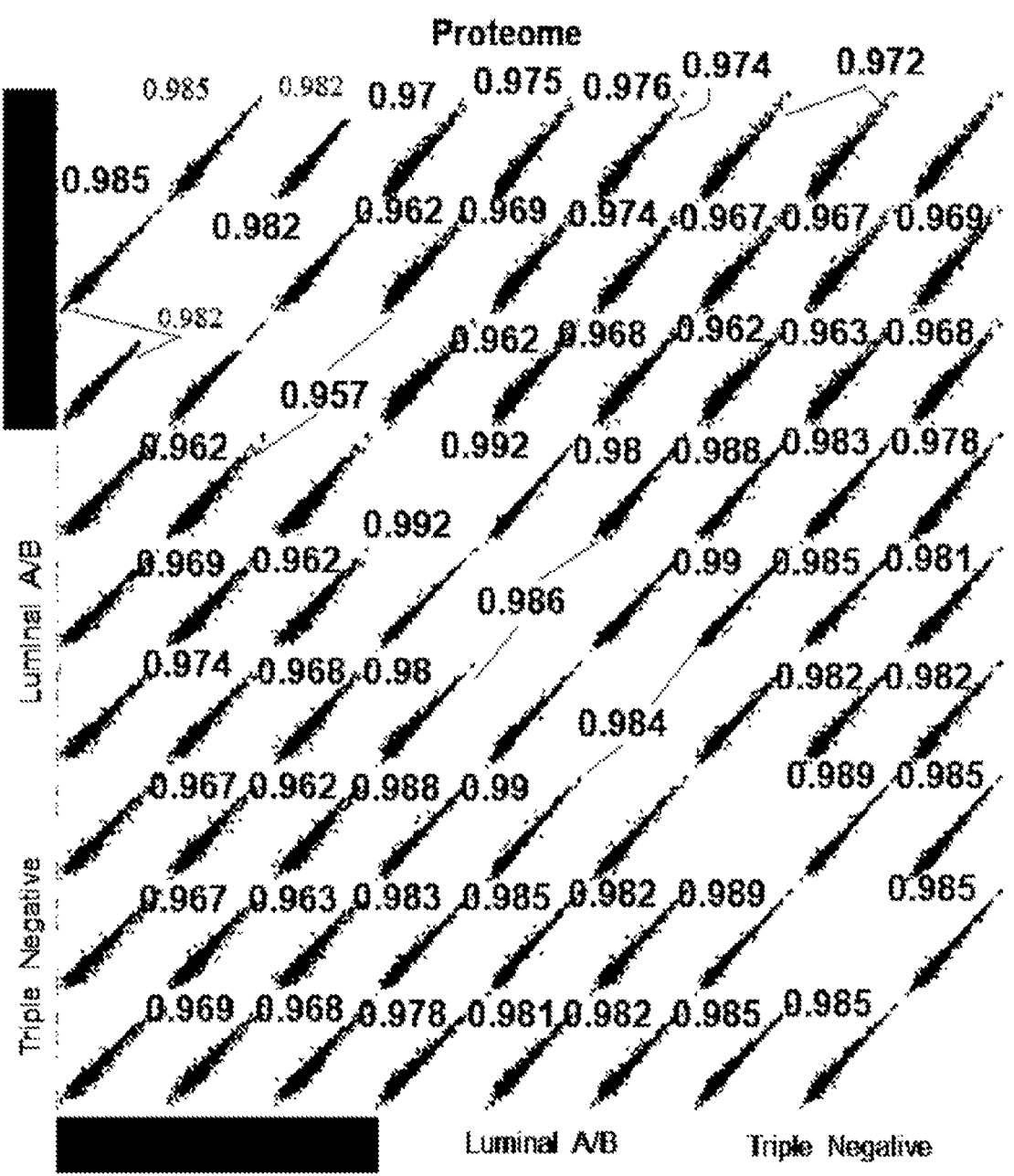
FIGS. 4A-4D show a multi-scatter plot of averaged profiles among the three groups and Pearson correlation coefficients depicting the log-2 transformed intensities of peptides from MaxQuant and Perseus for each modification: proteome (FIG. 4A), phosphorylation (FIG. 4B), acetylation (FIG. 4C), and glycosylation (FIG. 4D)
Figure 4B:
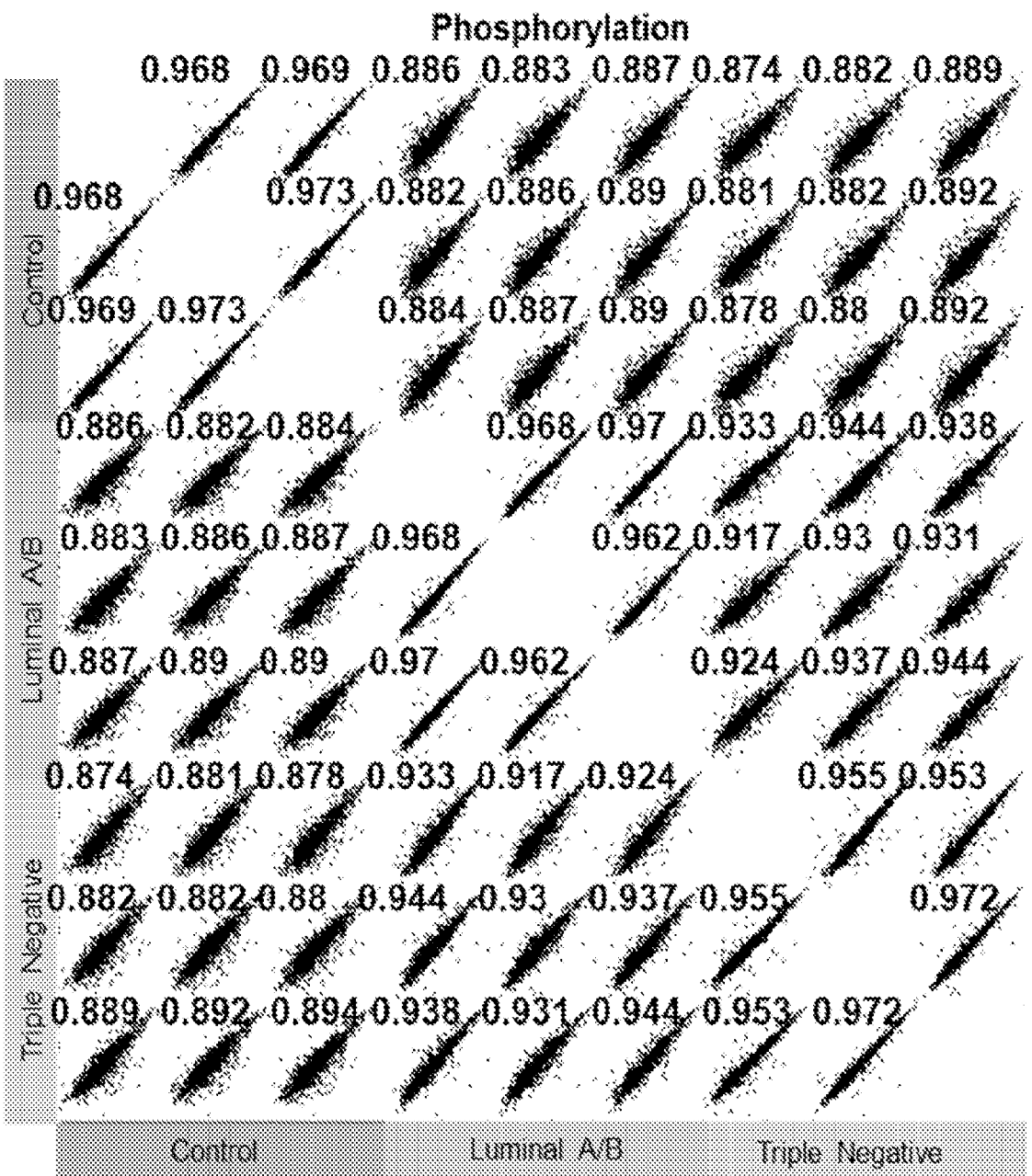
Figure 4C:
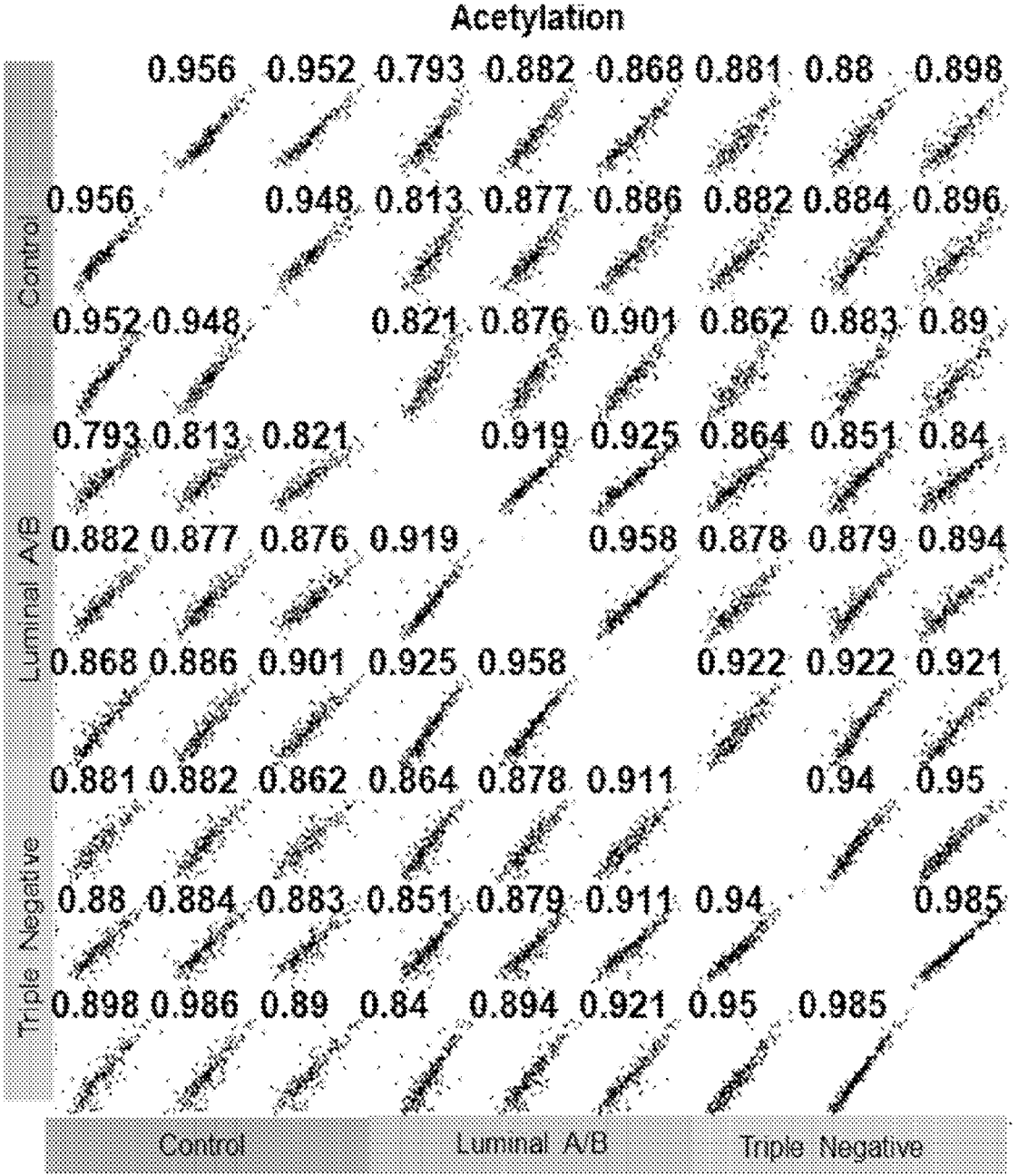
Figure 4D:
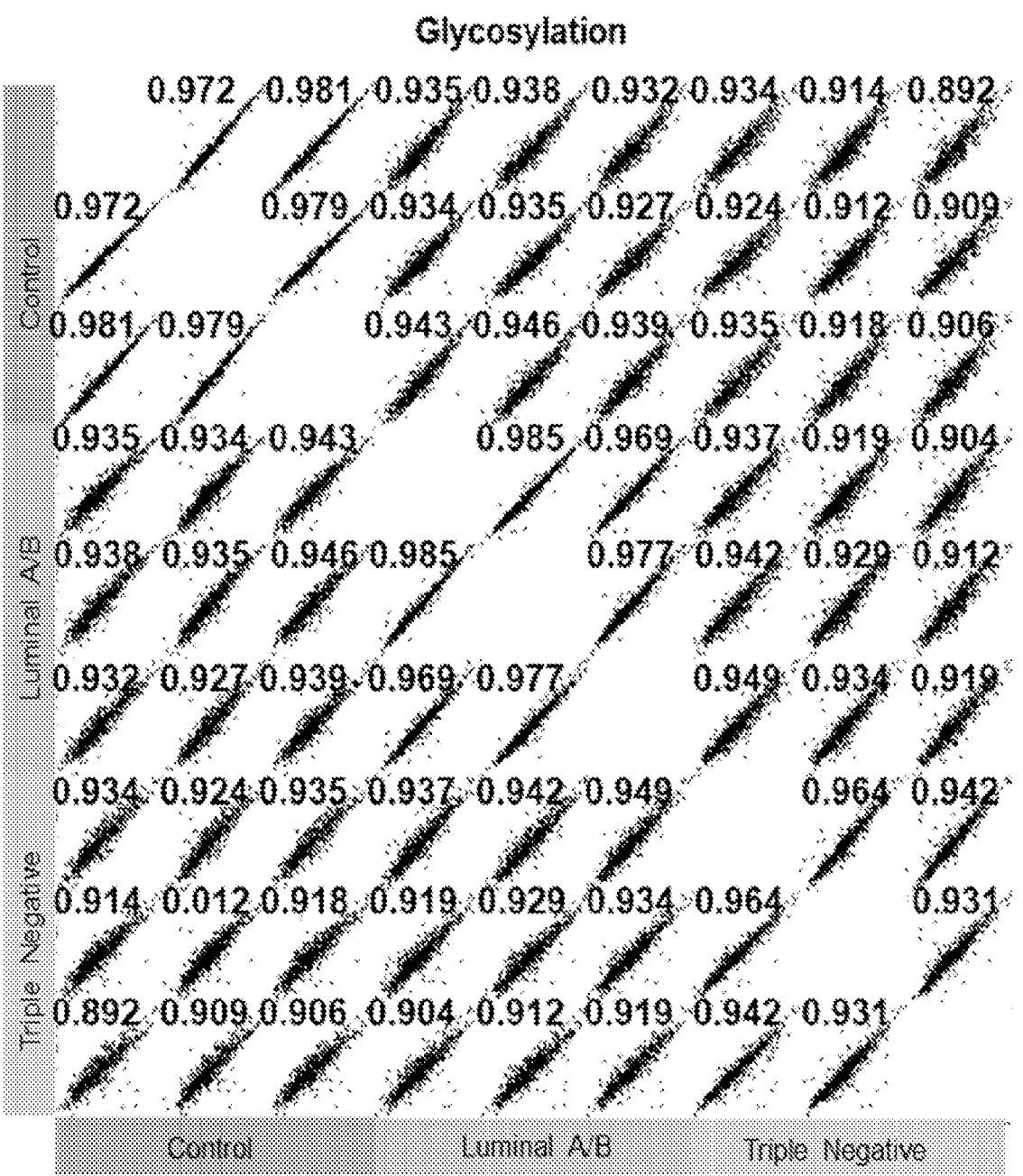

Now referring to FIGS. 3A and 3B, FIG. 3A is flow chart of the main strategy of workflow 300 and comprises 1) an unbiased discovery phase 302; and 2) a targeted verification and clinical validation phase 304, and FIG. 3B is a workflow of unbiased discovery phase 302. The objective of the unbiased discovery phase 302 was to identify relevant/candidate target biomarkers from PTMs. This phase 302 consisted of pooling plasma samples from each category (health control or breast cancer subtype) and analyzing any commonalities in each PTM using label-free quantification. Once a preliminary list of potential targets was obtained at step 302, such potential targets were verified through targeted proteomics (PRM) at step 304 using individual samples taken from breast cancer patients diagnosed with luminal A/B breast cancer or triple negative breast cancer. More specifically, the potential targeted biomarkers were input into a mass spectrometer for quantification and, thereafter, at clinical validation step 304, the expression profiles of the PTMs of the test pools were compared against individual samples taken from diagnosed patients to identify which candidate proteins were present with each condition. From this data, a PTM panel was prepared identifying which PTM expression patterns correlate with each subtype of breast cancer.

Plasma Samples

In the global PTM-ome experiment (workflow 300), at step 310, for initial screening, blood plasma samples were collected and pooled from healthy females (the Healthy Control group, n=20) (obtained through Susan G. Komen Tissue Bank; labeled "Healthy Control" in FIG. 3B) and from each subtype of breast cancer patients (the Luminal A/B group, n=20, and the TNBC group, n=20) (obtained through the University of Iowa Carver College of Medicine biobank; labeled "Luminal A or B" and "Triple Negative" in FIG. 3B). Each group pool (i.e. Healthy Control, Luminal A/B, and TNBC groups) had a final volume of 5 ml, from which 0.250 mL were collected from each patient. Plasma samples were collected by standard protocol and, in brief, the processing of each plasma sample was initiated within 30 min of blood draw to an ethylenediaminetetraacetic acid (EDTA) containing tube.

EVs Isolation

At steps 322 and 324, the plasma samples were centrifuged (322) and the EVs isolated (324) according to the reported protocol. EVs were isolated from human plasma through high speed and ultra-high-speed centrifugation (322). The samples were each spun for 30 min at 3500 rpm to remove all cellular debris and platelets. Thereafter, two steps of ultrahigh speed centrifugation were performed— plasma samples were centrifuged at 20,000×g at 4° C. for 1 hr—and the resulting pellets were washed with cold PBS and again centrifuged at 20,000×g at 4° C. for 1 hr. The resulting pellets collected were microvesicles (group 1).

Supernatant of the first centrifugation was further centrifuged at 1000,000×g at 4° C. for 1 hr. Pellets were washed with cold PBS and centrifuged again at 100,000×g for 1 hr. The pellets isolated from the ultrahigh-speed centrifugations were exosome particles (group 2). After isolation, the two separate groups of isolated EVs were combined, and the EVs were lysed and extracted (324).

Protein Digestion

After lysis of EVs and protein extraction, at step 326, peptides were enzymatically digested using LysC and trypsin with the aid of phase-transfer surfactants for better digestion efficiency and fewer missed tryptic sites. More specifically, EVs were solubilized in lysis buffer containing 12 mM sodium deoxycholate (SDC), 12 mM sodium lauroyl sarcosinate (SLS) and phosphatase inhibitor cocktail (Sigma-Aldrich, St. Louis, Mo.) in 100 mM Tris-HCL, pH 8.5. Proteins were reduced and alkylated with 10 mM tris-(2-carboxyethyl)phosphine (TCEP) and 40 mM chloro-acetamide (CAA) at 95° C. for 5 min. Alkylated proteins were diluted to 5-fold by 50 mM triethylammonium bicarbonate (TEAB) and digested with Lys-C in a 1:100 (w/w) enzyme-to-protein ratio for 3 hr at 37° C. Trypsin was added to a final 1:50 (w/w) enzyme-to-protein ratio for overnight digestion. The digested peptides were acidified with trifluoroacetic acid (TFA) to a final concentration of 0.5% TFA, and 250 µl of Ethyl acetate was added to 250 µl of the digested solution. The mixture was shaken for 2 min, then centrifuged at 13,200 rpm for 2 min to obtain aqueous and organic phases. The aqueous phase was collected and desalted using a 100 mg of Sep-pak C18 column.

Sequential PTMs Peptides Enrichment

At step 328, sequential PTM enrichment was performed to each pooled sample, starting with tyrosine phosphorylation 352 using PT66 antibody, followed by lysine acetylation 354, S/T phosphorylation 356 by PolyMAC and glycopeptide enrichment 358 using a hydrazide chemistry approach. Three technical replicates were performed.

Tyrosine Phosphopeptides Enrichment.

To immunoprecipitated phosphotyrosine containing peptides, the desalted peptides were resuspended in 50 mM Tris-HCL, pH 7.5. The samples were then added to anti-phosphotyrosine antibody beads (PT66) at a ratio of 30 µL of bead slurry for 1 mg of protein and incubated at 4° C. overnight with rotation. The PT66 beads were then washed sequentially with three solutions of lysis buffer (1) 50 mM Tris-HCL, 2) 50 mM NaCl, and 3) 1% NP40, pH 7.5) and water, three times per solution for 10 min each, with rotation, to wash off non-specific binding. The beads/tyrosine phosphopeptides were then sequentially incubated twice with different eluents: 1) with 0.1% TFA for 10 min, and 2) with 0.1% TFA in 50% ACN for 10 min. All eluates were thereafter removed and dried completely under vacuum for secondary enrichment with PolyMAC-Ti.

Lysine Acetylation Peptides Enrichment.

Immunoaffinity enrichment of lysine acetylated peptides from EVs was performed using the PTMScan protocol as described previously with some modification. In brief, 20 µl of lysine acetylation antibody conjugated beads were washed extensively with PBS. The flow-through from tyrosine phosphopeptides was mixed with lysine acetylation antibody beads and incubated for 2 hr at 4° C. The beads were washed twice with IAP buffer (50 mM MOPS, pH 7.2, 10 mM sodium phosphate, 50 mM NaCl) and three times with water. Peptides were eluted from beads with 0.15% TFA (sequential elutions of 55 µl followed by 50 µl, 10 min each elution at room temperature). Eluted peptides were desalted by SDB-XC stage tip and eluted with 40% acetonitrile in 0.1% TFA. Eluted peptides were dried under vacuum. The flow-through was also desalted by SDB-XC stage tip and dried under vacuum.

Polymer-Based Metal Ion Affinity Capture (PolyMAC) Phosphopeptides Enrichment.

From the flow-through resulting from the lysine acetylation step, peptides were resuspended in 200 µL of loading buffer containing 1% TFA and 80% acetonitrile, and incubated with PolyMAC-Ti silica beads for 15 min at room temperature pursuant to PolyMAC commercial protocols (e.g., 100 µg peptides per 50 µL PolyMAC bead slurry). The beads were loaded into the tip with frit to remove the flow-through. The beads were washed 1) twice with 200 µL washing buffer containing 100 µM glycolic acid, 1% TFA, and 50% ACN; and 2) once with 80% ACN, using centrifuge at 100 ref. The phosphopeptides were then eluted from the bead-bound PolyMAC-Ti by washing twice with 50 µL of 400 mM ammonium hydroxide, 50% ACN, using centrifuge at 100 ref. All eluates were collected and dried completely under vacuum. The flow-through was dried for subsequent glycopeptides enrichment.

Glycopeptides Enrichment.

Using the flow-through from the PolyMAC step, glycopeptides enrichment was performed according to the reported protocol. Desalted peptides were oxidized with 10 mM sodium periodate in 50% ACN, 0.1% TFA at room temperature with shaking in the dark for 30 min. Excess sodium periodate was quenched by using 50 mM sodium sulfite for 15 min at room temperature with shaking in the dark. The digested and oxidized samples were then mixed with 50 μL/100 μL hydrazide magnetic beads for individual and pooled samples, respectively. The mixture of magnetic beads and oxidized peptides was incubated over night with vigorous shaking at room temperature for the coupling reaction.

After coupling of the glycopeptides, to remove any non-coupled peptides, the beads were washed sequentially using 400 μL/800 μL of 50% ACN, 0.1% TFA and 1.5 M NaCl for individual and pooled samples, respectively, three times per solution for 1 min per wash. The beads were rinsed once with 100 μL/200 μL of 1× GlycoBuffer 2 (NEB) for individual and pooled samples, respectively, and incubated with 3 μL/4 μL of PNGase F (NEB) in 100 μL/200 μL GlycoBuffer 2 (NEB) for individual and pooled samples, respectively, to cleave the N-glycans for 2 hours at 37° C. Glycopeptides were eluted and beads were washed once with 100 μL/200 μL GlycoBuffer 2 (NEB) for individual and pooled samples, respectively. Both eluates were kept and desalted using SDB-XC StageTips. The released former N-glycopeptides were analyzed by liquid chromatography-tandem mass spectrometry (LC-MS/MS).

LC-MS/MS

At step 330, samples were analyzed by LC-MS/MS on a high-speed and high-resolution mass spectrometer with technical replicates, and label-free quantification of peptides was performed with a probability score of a modification site location over 0.75 to determine differential PTMs protein expression in plasma-derived EVs between the Healthy Control group sample and the breast cancer samples: Luminal A/B group and TNBC group (i.e. using a standard database).

More specifically, the PTMs peptides were dissolved in 4 μL of 0.3% formic acid (FA) with 3% ACN and injected into an Easy-nLC 1200 (Thermo Fisher Scientific). Peptides were separated on a 45 cm in-house packed column (260 μm OD×75 μm ID) containing C18 resin (2.2 μm, 100 Å, Michrom Bioresources) with a 30 cm column heater (Analytical Sales and Services) set to 50° C. The mobile phase buffer consisted of 0.1% FA in ultra-pure water (buffer A) with an eluting buffer at 0.1% FA in 80% ACN (buffer B) run over either with a 45 min or 60 min linear gradient of 5%-25% buffer B at a flow rate of 300 nL/min. The Easy-nLC 1200 was coupled online with a Thermo Scientific® Orbitrap Fusion™ Tribrid™ mass spectrometer. The mass spectrometer was operated in the data-dependent mode where the 10 most intense ions were subjected to high-energy collision dissociation (HCD) fragmentation (normalized collision energy (NCE) 30%, AGC 3e4, max injection time 100 ms) for each full MS scan (from m/z 350-1500 with a resolution of 120,000 at m/z 200).

This platform identified 2,693 proteins, 1,764 phosphoroteins, 504 N-glycoproteins, and 331 acetylated proteins (collectively, the "Identified EV Proteins") with a pipeline that allowed for the enrichment of three PTMs from the same biological sample.

Data Processing and Verification

In the subsequent analysis to identify a preliminary list of potential targets and verify that the high-speed and ultra-highspeed centrifugation isolation method previously described (step 302) was suitable for downstream PTM-omics, the raw files were searched against multiple databases at step 304. Primarily, the Identified EV Proteins were overlapped against a EV-curated database downloaded from Vesiclepedia, a publicly available compendium of extracellular vesicle data. This comparison verified the EV isolation was high using the presently described protocols (i.e. performed to verify EV isolation efficiency, with over a 70% overlap).

The Identified EV Proteins were also compared directly against the Uniprot Knowledgebase database (version August 2017), which is a publicly available, central hub for the collection of functional information on proteins, with no redundant entries for peptide and protein identification. Importantly, the data from this database is drawn from tissue samples (i.e. obtained through biopsies), and the quantitative comparison results confirmed a subset of the Identified EV Proteins corresponded with markers in the tissue biopsies.

After differential intensities at the modification site level were selected, the corresponding precursor peptides were selected and imported into Skyline (Pino, L. J. et al, 2017). Quantification was also performed using the Andromeda peptide search engine integrated into the MaxQuant software environment (version 1.5.6.1) for the analysis of raw mass spectrometry data. In other words, at this step, the raw mass spectrometry data of the samples were matched to peptide sequences in the Andromeda database subject to the user-defined parameters set forth below, which generated a spectral library against which the raw data was used to visualize the extracted ion chromatograms.

More specifically, initial precursor mass tolerance was set to 20 ppm, the final tolerance was set to 6 ppm, and ITMS MS/MS tolerance was set at 0.6 Da. Search criteria included a static carbamidomethylation of cysteines (+57.0214 Da) and variable modifications of (1) oxidation (+15.9949 Da) on methionine residues, (2) acetylation (+42.011 Da) at N-terminus of protein, and (3) phosphorylation (+79.996 Da) on serine, threonine or tyrosine residues for phosphorylation, acetylation (+42.011 Da) on lysine residue for acetylation and deamidation (+0.984 Da) on asparagine residues for glycosylation were searched. The search was performed with Trypsin/P digestion and allowed a maximum of two missed cleavages on the peptides analyzed from the sequence database. The false discovery rates of proteins, peptides and PTMs sites were set at 0.01. The minimum peptide length was six amino acids, and a minimum Andromeda score was set at 40 of modified peptides. The glycosylation sites were selected based on the matching to the N-X-S/T (X not Pro) motif. A site localization probability of 0.75 was used as the cut-off for localization of modification sites. All of the peptide spectral matches and MS/MS spectra are available through MaxQuant viewer. All the localized modification sites and corresponding proteins were submitted to pLogo software and Panther to determine the modification motifs and gene ontology, respectively.

After removing peptides that were detected as differential due to erroneous extracted ion chromatograph integration (XIC) by MaxQuant, the list of target peptides was further refined by removing the sequences that contained more than 3 amino acids that could carry the respective modification (STY for phosphorylation, K for acetylation, and N for glycosylation), ragged tryptic ends, sequences longer than 25 amino acids or any histidine. Precursor ions m/z's were collapsed for phosphor-isoforms and additional filtering was done to fit the desired duty cycle of 2.5 seconds with an injection time of 100 ms for each MS2 scan for glycol-peptides and acetylated peptides, or 50 ms for phosphopeptides, with a retention time window of 5 min before the minimum observed retention time and 5 min after the highest observed. This process was performed manually, giving priority to the peptides that exhibited the highest observed difference in intensities between conditions.

Quantitative Data Analysis and Biomarkers for Breast Cancer Subtype Classification Quantitative analysis of EV proteome, phosphoproteome, N-glycoproteome, and acetylproteome was performed between the Healthy Control, Luminal A/B, and TNBC groups. All data was analyzed using Perseus software (version 1.5.4.1), which provides a comprehensive portfolio of statistical tools for high-dimensional omics data analysis, including the detection of predictive protein signatures.

For quantification of both proteomic and PTM-omic datasets, the intensities of proteins and sites of the PTMs were both derived from MaxQuant, and any missing values of intensities were replaced by normal distribution with a downshift of 1.8 standard deviations and a width of 0.3 standard deviations. The significantly increased PTMs sites or proteins in patient samples were identified by ANOVA multi-test with a permutation-based FDR cut-off of 0.05 for all datasets. For heatmap modalities, the changed sites or proteins were used, per standard, grouped together based on similarity of their gene expression patterns, with the imputed dataset was normalized by z-score within each dataset.

FIGS. 4A-4D illustrate the quantitation results from MaxQuant and Perseus showing Pearson correlations across breast cancer subtypes (the Luminal A/B and TNBC groups) and healthy controls (the Healthy Control group), replicates and modification. The scatterplots and Pearson correlation coefficients depicting the log-2 transformed intensities of peptides from each modification in triplicates across each condition.

Figures 5A, 5B:
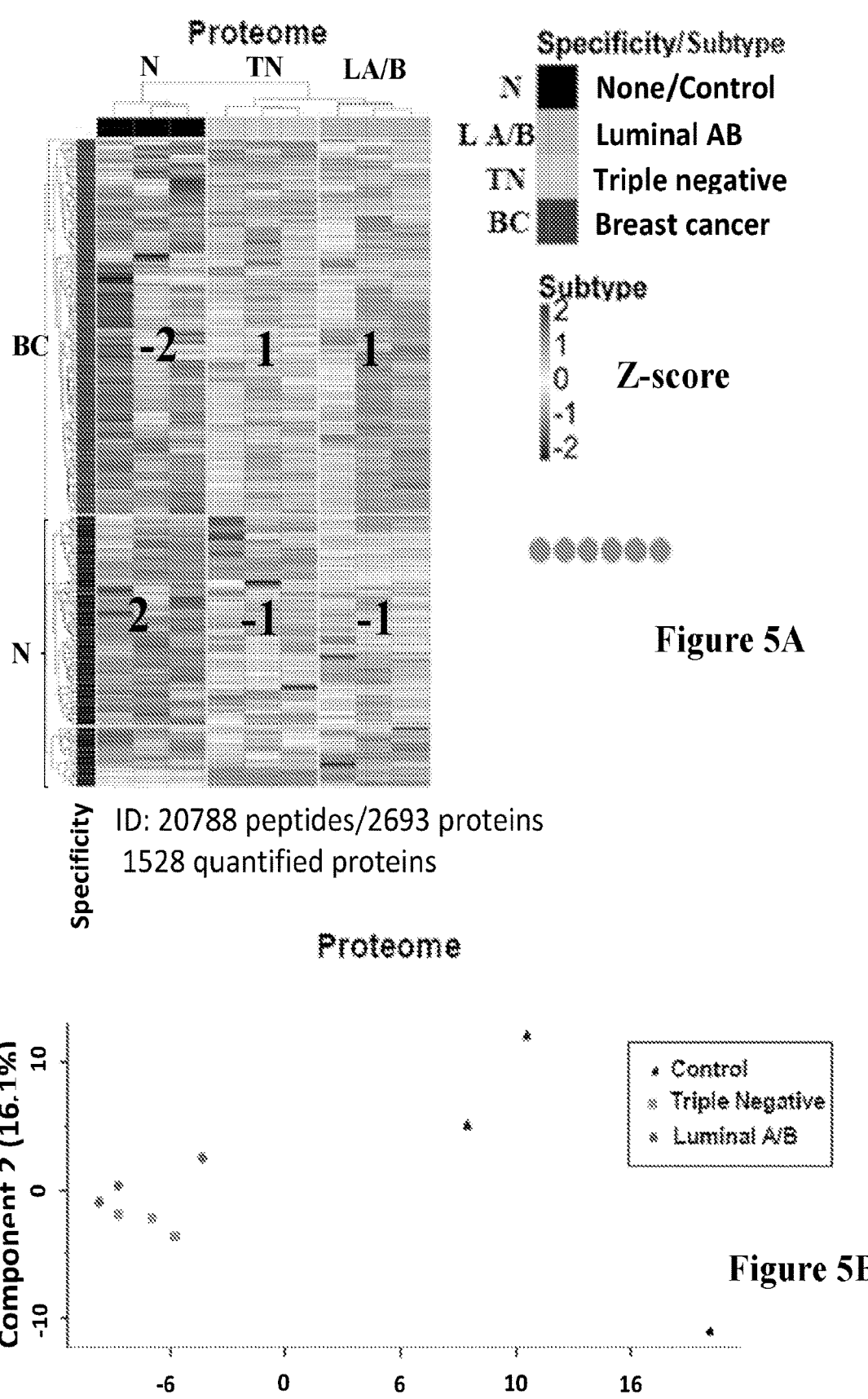
FIG. 5A shows a heatmap representing the quantitative analysis of the proteome depicting each condition (imputed data set was normalized by z-score which shows red as 2 and blue as –2)
FIG. 5B shows graphical data resulting from a principal component analysis (PCA) of the proteome in a 2D graph of PC1 and PC2.

FIG. 5A indicates the majority of changed proteins were enriched in all breast cancer subtypes (i.e. both in the Luminal A/B and TNBC groups), instead of being subtype-specific. This supports that global proteomic analysis alone will not provide sufficient information about differentiation between breast cancer subtypes.

Figures 6A, 6B:
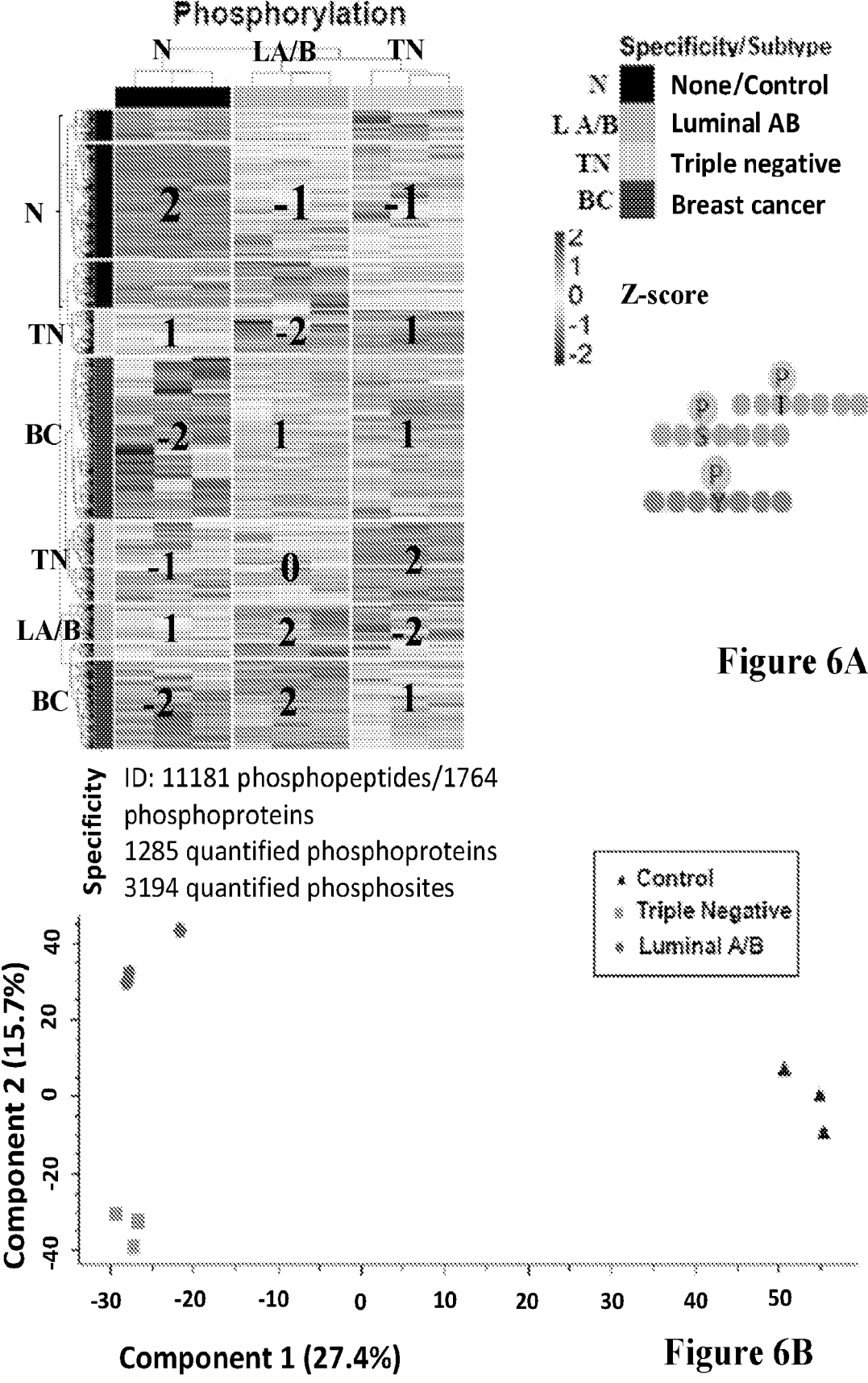
FIG. 6A shows a heatmap representing the quantitative analysis of the phosphoproteome depicting each condition (imputed data set was normalized by z-score which shows red as 2 and blue as –2)
FIG. 6B shows graphical data resulting from a PCA of the phosphorylation modification in a 2D graph of PC1 and PC2.
Figures 7A, 7B:
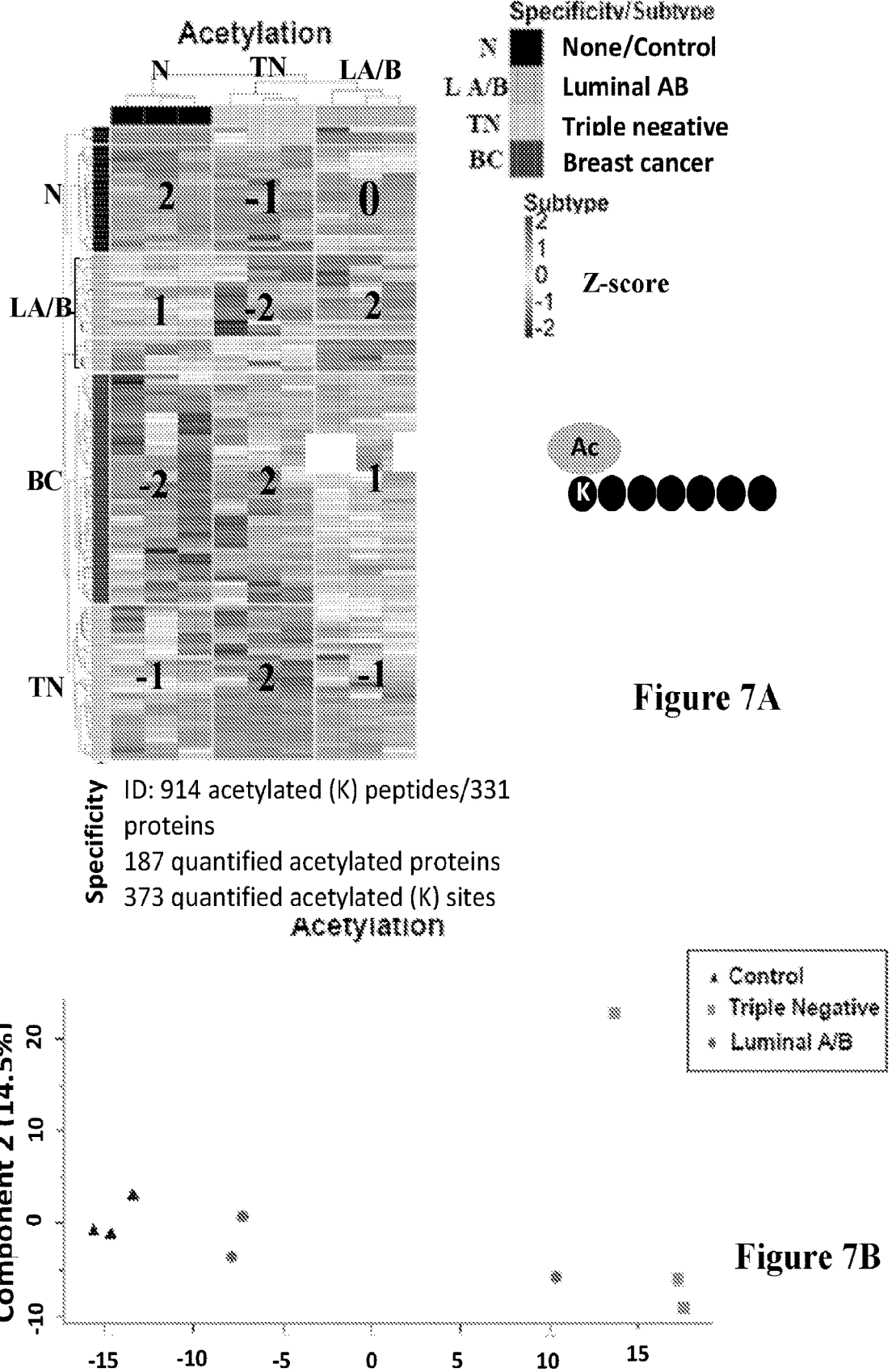
FIG. 7A shows a heatmap representing the quantitative analysis of the acetylproteome depicting each condition (imputed data set was normalized by z-score which shows red as 2 and blue as –2)
FIG. 7B shows graphical data resulting from a PCA of the acetylation modification in a 2D graph of PC1 and PC2.
Figures 8A, 8B:
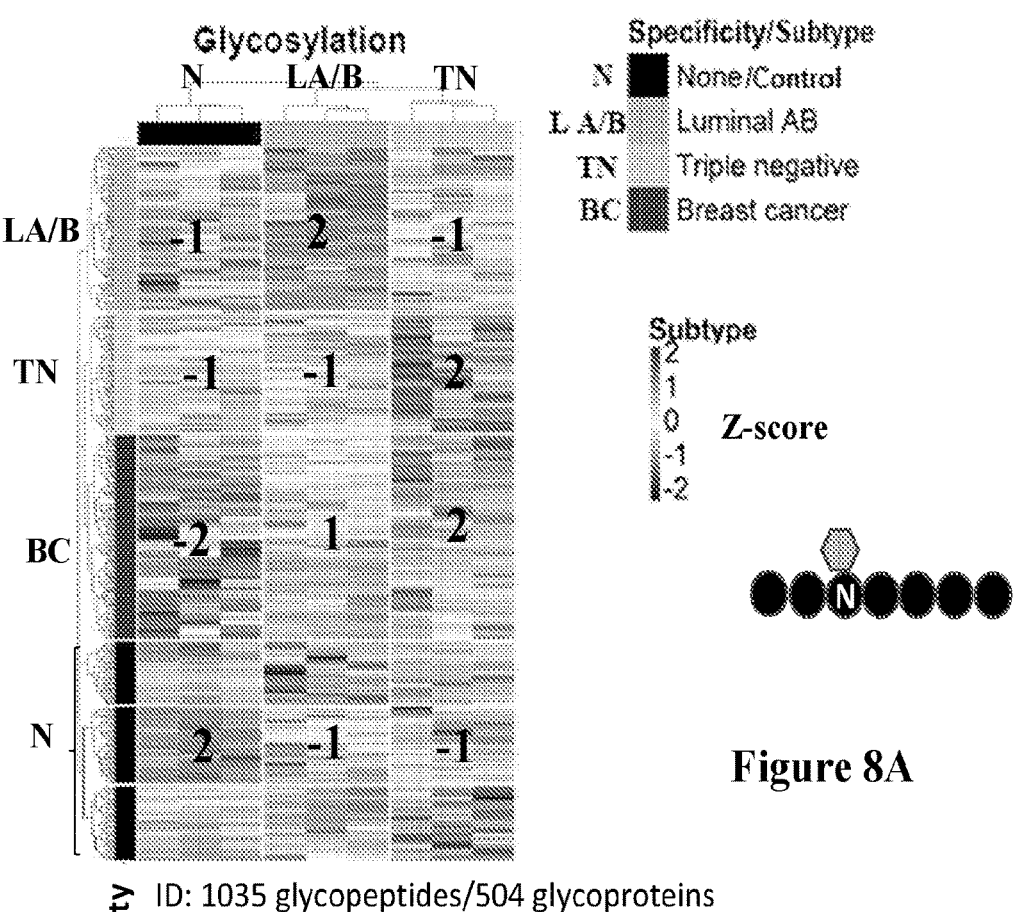
FIG. 8A shows a heatmap representing the quantitative analysis of the glycoproteome depicting each condition (imputed data set was normalized by z-score which shows red as 2 and blue as –2)
FIG. 8B shows graphical data resulting from a PCA of the glycosylation modification in a 2D graph of PC1 and PC2.

On the other hand, FIGS. 6A, 7A, and 8A show heatmaps representing the quantitative analysis of PTM-omics between breast cancer subtypes and healthy controls. Perhaps more specifically, these heatmaps show the differential expression of each PTM and indicate the clusters of candidate targets that are exclusive to (i.e. significantly increased in) each subtype of breast cancer. FIGS. 6A, 7A, and 8A support similar (albeit upregulated) expressions of phosphorylation, glycosylation, and acetylation between the Luminal A/B and TNBC groups as compared to the Healthy Control group, whereas improved distinctions across subtypes are visualized in the phosphoproteome, N-glycoproteome, and acetylproteome (as compared to the proteome) such that subtype-specific targets are distinguishable. This heatmap data was further utilized to select candidate targets from each PTM group that were able to best differentiate the subtypes.

Figure 6C:
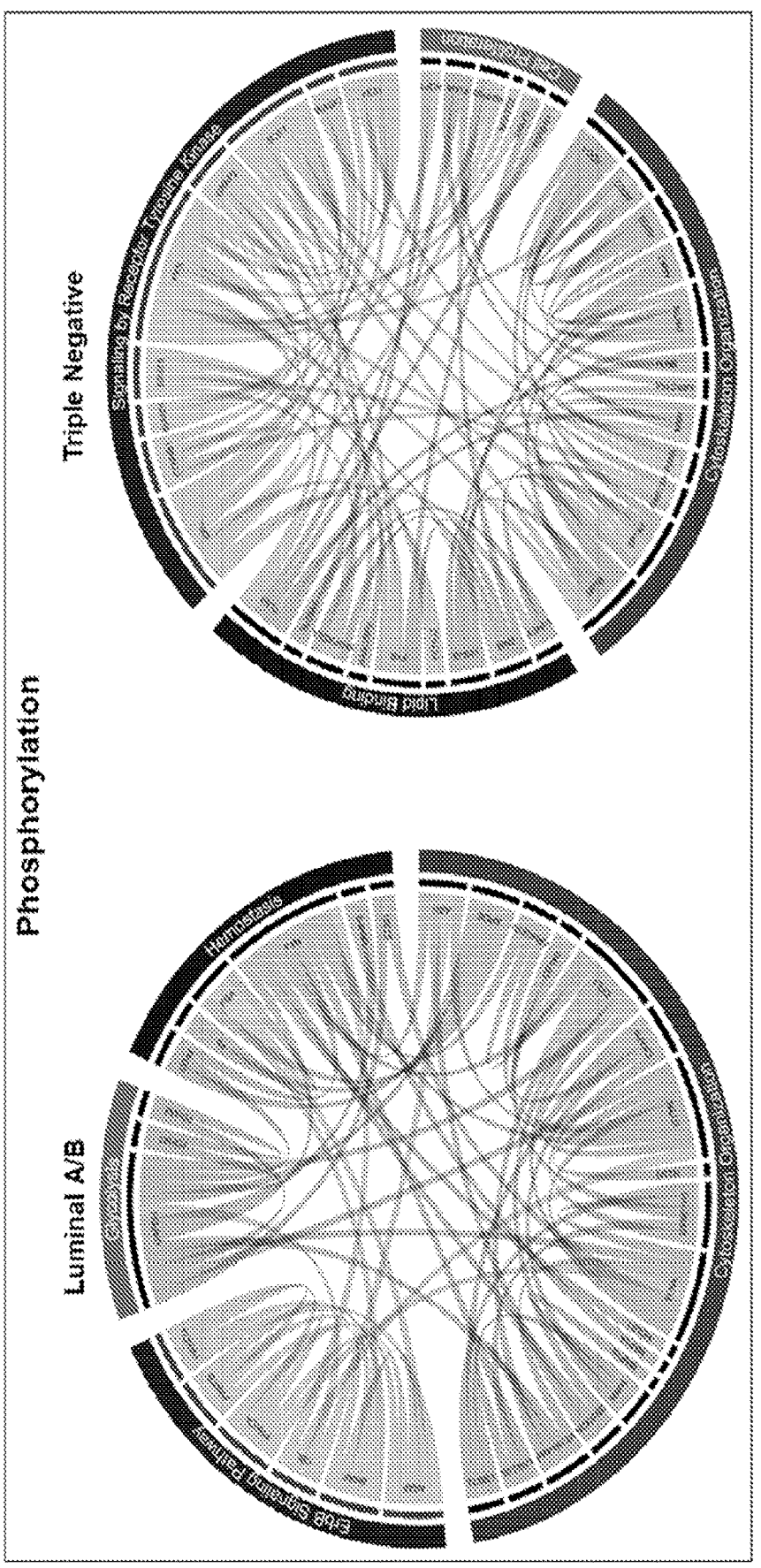
FIG. 6C shows a gene ontology circos plot analysis of upregulated proteins for phosphorylation modification.
Figure 7C:
FIG. 7C shows a gene ontology circos plot analysis of upregulated proteins for acetylation modification.
Figure 8C:
FIG. 8C shows a gene ontology circos plot analysis of upregulated proteins for glycosylation modification.

FIGS. 6C, 7C, and 8C show the gene ontology (GO) circos plot analysis of upregulated proteins in each modification (using R). GO analysis determines which terms are over-represented (or under-represented), with each connection between a gene and the condition represents the absolute fold change. In the present context, the GO results revealed metabolic pathways and PI3K-Akt signaling pathways, respectively, which supports lysine acetylation and abnormal glycosylation in the breast cancer samples (i.e. the Luminal A/B and TNBC groups). This is supported by conventional literature, which supports 1) metabolic pathways are strongly associated with lysine acetylation, and 2) abnormal protein glycosylation is activated in PI3K-Akt signaling pathways and Notch signaling pathways.

Further, FIGS. 5B, 6B, 7B, and 8B show the results of principal component analysis (PCA) performed on the proteome, phosphoproteome, acetyleproteome, and glycoproteome data, respectively. PCA is a statistical procedure used to visualize genetic distance and relatedness between samples and/or populations, with the overall purpose being to reduce the dimensionality of a dataset containing multiple variables. Here, PCA for the phosphoproteome analysis was far superior in distinguishing LAB and TNBC as compared to the global proteome analysis results. For the acetylproteome, variables were more distanced in the LAB, indicating better diagnostic potential at least as compared with TNBC, and in the N-glycoproteome both subtypes could have been better separated. Accordingly, the PCA data shows the reproducibility of each replicate, further confirms the ability of the each PTM to separate the different disease subtypes, and indicates the phosphoproteome can better distinguish between breast cancer subtypes as compared to the other two modifications tested and the proteome.

In sum, quantitative analyses of EV proteomes reveal similar expressions between the Luminal A/B and TNBC groups as compared to controls (Healthy Control group), whereas better distinctions across subtypes were visualized in the phosphoproteome, N-glycoproteome, and acetylproteome where subtype-specific targets were more readily distinguishable (such targets being selected to advance to the targeted proteomics study described below). This further indicates that these PTM differences between breast cancer subtypes and controls are not merely a result of differences in protein expression, therefore, justifying the need to develop PTM-omics approaches to deeper analyze truly specific events with breast cancer patients.

As a notable example, programmed death ligand 1 (PD-L1) was identified in both phosphoproteome and N-glycoproteome data, and was significantly increased in TNBC patients as compared to the Luminal A/B and Healthy Control groups. PD-L1 has been found to be abundant in cancer cells and in breast cancer, specifically, in TNBC patients, which further supports PTM-omics approaches and the potential of EVs as relevant biomarkers.

The data in Tables 1 and 2 summarizes the results of the aforementioned analyses (Table 1):

TABLE 1

| | | Identified Unique Modifications | | | |
|---|---|---|---|---|---|
| Total Proteomics | 20,788 peptides | 2,693 proteins | 1,528 quantified proteins | | FIGS. 7A-7B |
| Phosphoproteomics | 11,181 phosphopeptides | 1,764 phosphoproteins | 1,285 quantified phosphoproteins | 3,194 quantified phosphosites | FIGS. 8A-8C |
| N-glycoproteomics | 1,035 glycopeptides (that matched motif (N-X-S/T) | 504 glycoproteins | 481 quantified glycoproteins | 1,078 quantified glycosites | FIGS. 9A-9C |

TABLE 1-continued

Figures 10A, 10B:
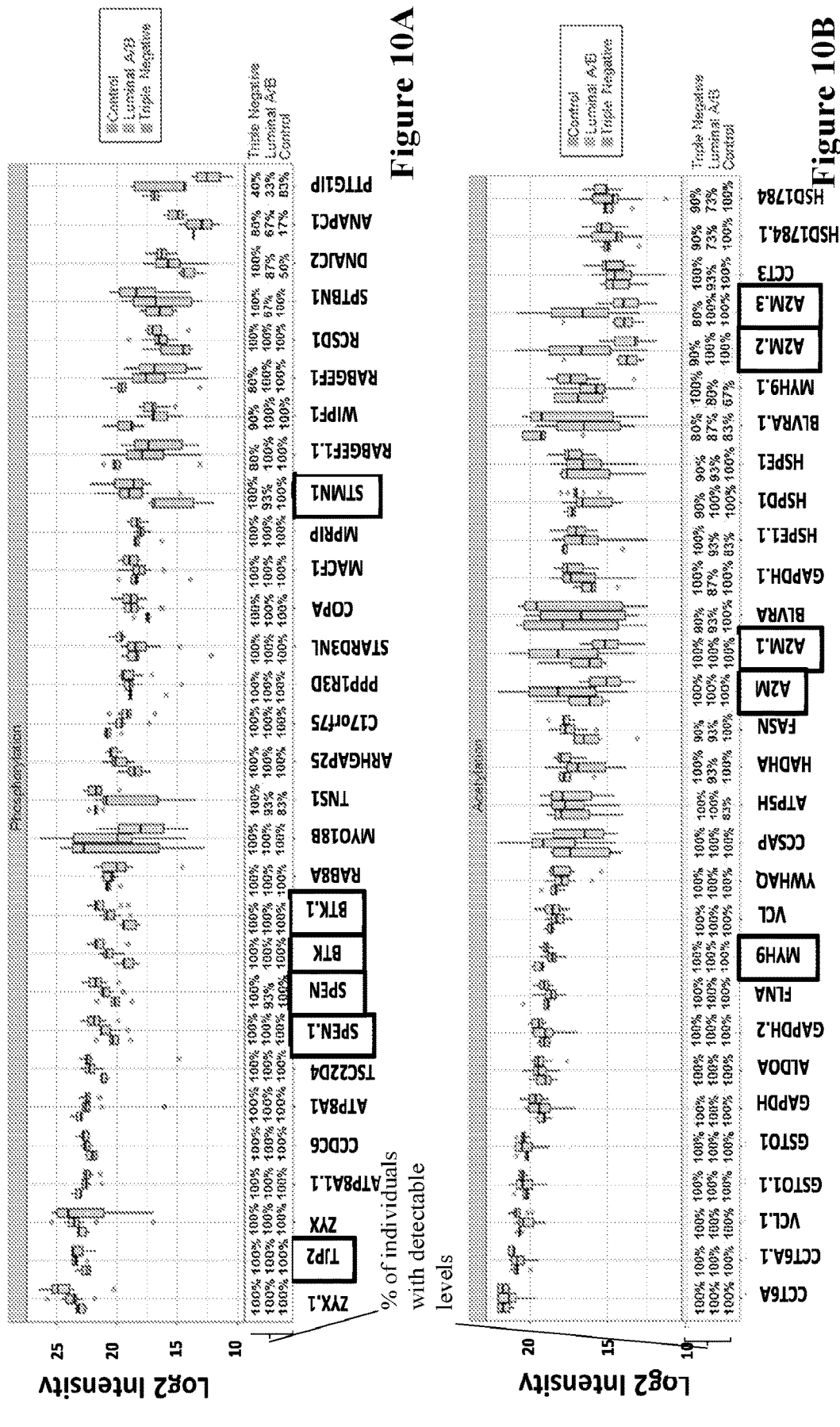
FIGS. 10A-10C show boxplots of the top 30 identified targets from the targeted proteomics strategies set forth herein, per modification, and showing percentages of individuals with detectable levels, with FIG. 10A relating to phosphorylation, FIG. 10B relating to acetylation, and FIG. 10C relating to glycosylation, and all of which have the results listed per gene in the order of Control, Luminal A/B, and Triple Negative.
Figure 10C:
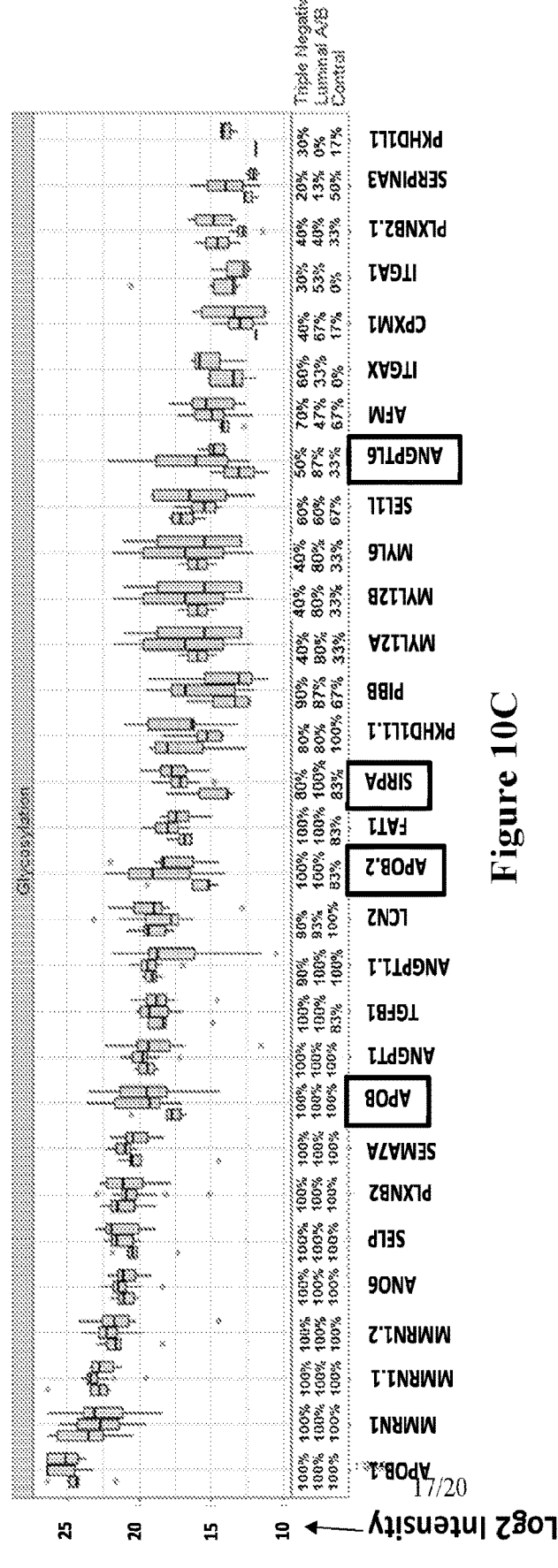

| Identified Unique Modifications | | | | | |
|---|---|---|---|---|---|
| Acetyleproteomics | 914 acetylated (K) peptides | 331 proteins | 187 quantified acetylated proteins | 373 quantified acetylated (K) sites | FIGS. 10A-10C |

Since certain PTM-sites were significantly enriched using the described protocols, such sites were quantified and thereafter the peptide, protein and gene to which they belong were identified and quantified. As not all peptides are quantifiable, statistical analysis was performed to filter those out of the results.

Targeted Proteomics—Analysis of Candidate Markers

After the first screening phase was performed with the pooled samples between the Healthy Control, Luminal A/B, and TNBC groups (step 302), a group of target-specific makers were selected per modification and breast cancer subtypes (see Table 2A) and verified at step 304 as breast cancer subtype markers through targeted proteomics. Because breast cancer is extremely heterogeneous, the chance of identifying a single diagnostic biomarker for each subtype is not likely. Instead, the identification of a panel of candidate biomarkers that reflect the onset and progression of key breast cancer subtype-related signaling events is more feasible.

Further, because modification-specific antibodies suitable for construction of ELISA are typically not easily available, phase 304 of workflow 300 involved targeted, quantitative MS approaches such as parallel reaction monitoring (PRM) and multireaction monitoring (MRM) are beneficial for validation.

TABLE 2A

| Selected Targets | | | | |
|---|---|---|---|---|
| | Breast Cancer (LAB and TNBC) | Luminal A/B (LAB) | Triple Negative (TNBC) | Selected for Targeted Approach |
| Specific phosphosites | 450 | 108 | 141 | 135 phosphopeptides |
| Specific glycosites | 185 | 112 | 74 | 98 glycopeptides |
| Specific acetylated sites | 34 | 21 | 28 | 47 acetylpeptides |

135 phosphopeptides, 98 glycoproteins, and 47 acetylated peptides were selected from step 302 and, the differential modifications of the selected markers were verified in patients with different subtypes of breast cancer, using scheduled PRM to quantify individual EV modifications in plasma using 44 individual samples from patients experiencing Luminal A/B subtype (n=20) ("LAB"), TNBC subtype (n=15) ("TNBC"), and healthy individuals (n=9) ("Control") (all obtained through the University of Iowa Carver College of Medicine biobank; 700 μL plasma per sample).

Preparation was performed according to the protocols described above in connection with the pooled samples; however, the MS analysis was targeted with the selected targets identified in Table 2A and Table 2B (below). Perhaps more specifically, samples taken from patients were analyzed in conjunction with the previously data-dependent results described above to validate which of the targeted/candidate proteins are clinically present within the biofluid sample taken from the patients/individuals with each condition.

Methodology Validation.

As a demonstration that PRM can be used to initially verify candidate modifications, four phosphoproteins were selected: Ral GTPase-activating protein subunit alpha-2 (RALGAPA2), cGMP-dependent protein kinase1 (PKG1), tight junction protein 2 (TJP2), and nuclear transcription factor, X box-binding protein 1 (NFX1). These four proteins showed significant phosphorylation up-regulation in patients with cancer, were previously reported as phosphoproteins and have been implicated in multiple breast cancer studies. Quantitative assays based on PRM were performed with plasma EV samples from 13 patients with cancer (8 additional patient samples) and 7 healthy controls (one additional control). The relative abundance data of phosphopeptides from four individual proteins was assessed (not shown), with RALGAPA2, PKG1, and TJP2 observed to be significantly elevated in patients with breast cancer as compared with control patients. However, the fold difference was noticeably smaller in PRM than label-free quantification. Similar to the quantitative analyses data above, this study clearly indicates that EV PTMs can be readily captured and analyzed.

PRM Investigations; Identification of Biomarkers for Breast Cancer Classification.

Generally, PRM is an ion monitoring technique based on high-resolution and high-precision mass spectrometry and is useful for the absolute quantification of proteins and peptides, especially for the quantification of multiple proteins in a complex sample.

The 44 individual peptide samples were dissolved in 4 μL of 0.3% formic acid (FA) with 3% ACN and injected into an Easy-nLC 1200 (Thermo Fisher Scientific). Peptides were separated on a 45 cm in-house packed column (360 μm OD×75 μm ID) containing C18 resin (2.2 μm, 100 Å, Michrom Bioresources) with a 30 cm column heater (Analytical Sales and Services) set to 50° C. The mobile phase buffer consisted of 0.1% FA in ultra-pure water (buffer A) with an eluting buffer of 0.1% FA in 80% ACN (buffer B) run over either with a 45 min or 60 min linear gradient of 5%-25% buffer B at flow rate of 300 nL/min. The Easy-nLC 1200 was coupled online with a Thermo Scientific™ Orbitrap Fusion™ Tribrid™ mass spectrometer.

In all experiments, a full mass spectrum at 60,000 resolution relative to m/z 200 (AGC target 3E6, 100 ms maximum injection time, m/z 400-1600) was followed by up to 20 PRM scans at 15,000 resolution (AGC target 1E5, 50 ms maximum injection time) as triggered by a scheduled inclusion list. Higher-energy collisional dissociation (HCD) was used with 30 eV normalized collision energy. PRM data were manually curated with Skyline (version 3.5.0.9319).

The results generated a panel of 30 specific PTM sites that differentiate breast cancer subtypes. FIG. 9A shows the variable importance classification ranking of the top 30 classifiers that performed the best in distinguishing between the two breast cancer subtype (LAB and TNBC) and Control groups. Table 3 below provides a listing of the same, with there being 22 phosphorylated target biomarkers, 6 acetylated target biomarkers, and 2 glycosylated target biomarkers:

TABLE 3

| Biomarker PTM sites | |
| --- | --- |
| Phosphorylation markers | TJP2 (tight junction protein 2) |
| | CCDC6.1 (coiled-coil domain containing 6) |
| | ZYX and ZYX.1 (zyxin) |
| | ASAP1 (ankyrin repeat and pH domain 1) |
| | RAB7A (Ras-related protein Rab-7a) |
| | MYO18B (myosin 18B) |
| | ARHGAP25 (rho GTPase activating protein 25) |
| | STARD₃NL (STARD3 N-terminal like or mentho) |
| | SPTBN1 (spectrin beta, non-erythrocytic 1) |
| | TSC22D4 (TSC22 domain family member 4) |
| | SPEN and SPEN.1 |
| | (spen family transcriptional repressor) |
| | DNAJC2 (DNAJ heat shock protein family |
| | (Hsp40) member C2) |
| | TP8A1.1 (phospholipid-transporting ATPase IA) |
| | PRKCA (protein kinase C alpha) |
| | ANAPC1 (anaphase promoting complex subunit 1) |
| | STMN1 (stathmin 1) |
| | C17orf75 (chromosome 17 open reading frame 75) |
| | ATP8A1 (ATPase phospholipid transporting 8A1) |
| | TNS1 (tensin 1) |
| | WIPF1 (WAS/WASL |
| | interacting protein family member 1) |
| | BTK and BTK.1 (bruton tyrosine kinase) |
| Acetylation markers | CCT6A (chaperonin containing TCP1 subunit 6A) |
| | A2M.3, A2M.2, A2M.1, A2M |
| | (alpha-2-macroglobulin) |
| | MYH9 (myosin heavy chain 9) |
| Glycosylation markers | APOB (apolipoprotein B) |
| | SIRPA (signal regulatory protein alpha) |

Integrative determinations revealed that phosho.TNS1, phospho.WIPF1, phospho.C17orf75, phospho.ATP8A1, phospho.BTK.1, phospho.BTK, and acetyl.MYH9 are the most efficient of these 30 targets for accurate and consistent differentiation of breast cancer subtypes.

Similarly, the scatterplot in FIG. 9B depicts log-2 intensities of Bruton's Tyrosine Kinase (BTK), which is phosphorylated, and myosin-9 (MYH9), which is acetylated, which were identified as the top two classifiers to distinguish between breast cancer subtypes and the control groups, ranked in importance using random forest. BTK and MYH9 exhibited great potential on separating the Control group samples from LAB and TNBC (see FIG. 9A). These two target biomarkers could segregate the PRM individual samples, pursuant to their relative expression as compared to the Control. As shown in FIG. 9B, underexpression of MYH9 relative to the Control and concurrent overexpression relative to the Control is indicative of the subject experiencing the TNBC subtype; whereas underexpression of MYH9 and equivalent or higher expression of BTK, both relative to the control, is indicative of the subject experiencing the LAB subtype.

Figures 11A, 11B:
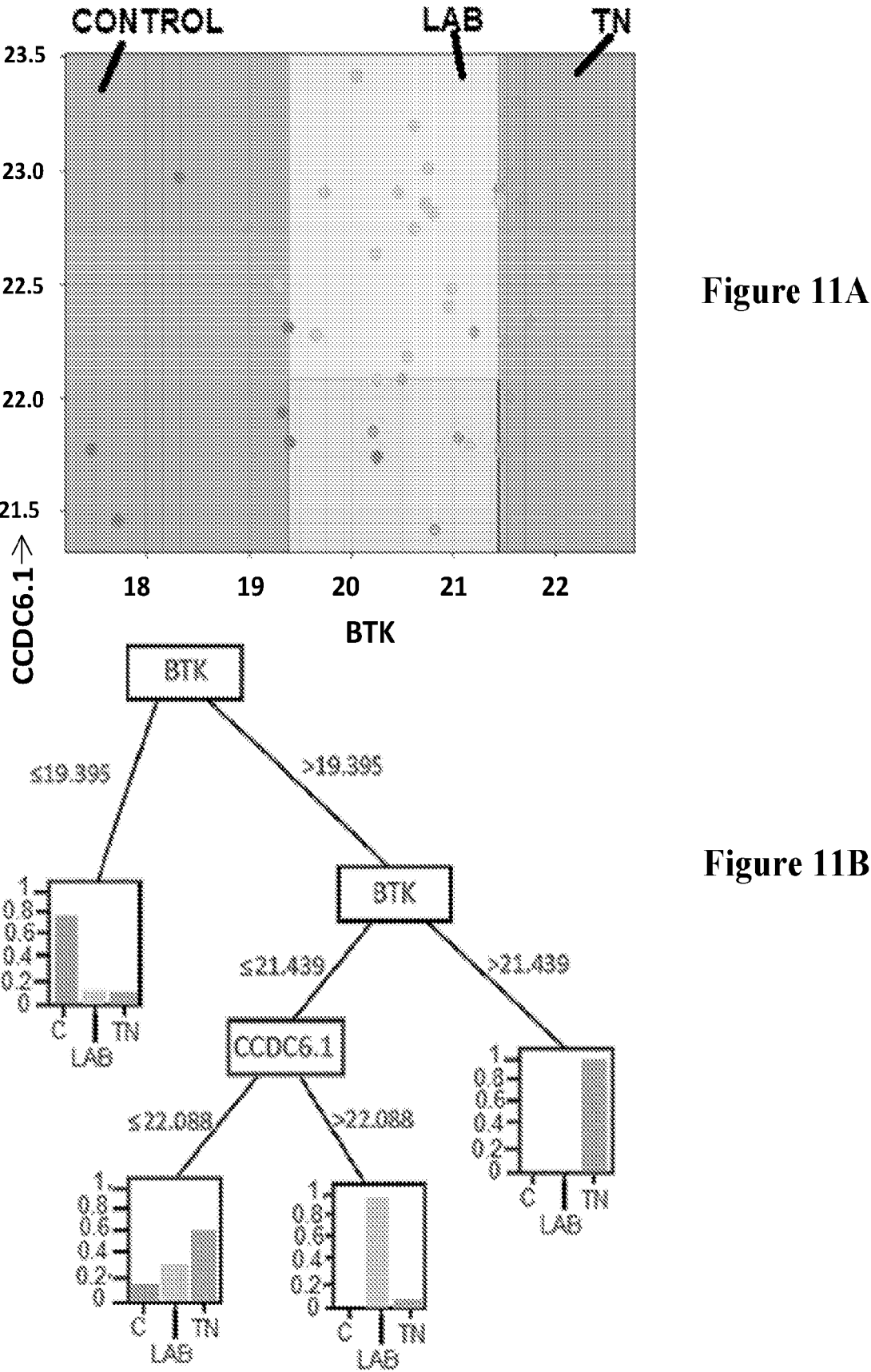
FIGS. 11A-11C show graphical data representative of the targeted approach to verifying phosphorylation sites as specific biomarkers of breast cancer subsets, including a decision tree representation of the biomarker expression results and resultant breast cancer subtype expression patterns identified by the research presented herein.

FIGS. 10A-10C show data of PTMs from the 30 individual target proteins per modification presented as boxplots and showing the percentages of detectable levels in each of the individual samples. FIG. 11A depicts log-2 mass spectrometric intensities of one phosphopeptide from coiled-coil domain-containing protein 6 (CCDCl6.1), and BTK, which as noted above is phosphorylated as well. As seen in FIG. 11A, while the Control may express high levels of CCDCl6.1, overexpression of BTK relative to the Control was indicative of TNBC. With reference from the figures, phospho.TJP2, and phospho.STMN1 were observed to be significantly elevated in patients with LAB (noting, however, that a number of these sites can also indicate the TNBC subtype where other PTMs are differentially expressed (FIG. 10A), phospho.CCDCl6.1, phospho.SPEN.1, phospho.BTK, phospho.SPEN, phospho.BTK.1 were observed to be significantly elevated in patients with TNBC (FIG. 10A), acetyl.A2M, acetyl.A2M.1, acetyl.A2M.2, and acetyl.A2M3 were all observed to be significantly and differentially elevated in patients with the LAB subtype (FIG. 10B), and glycol.ANGPTL6 was observed to be significantly elevated in patients with LAB (FIG. 10C) and both SIRPA and APOB are overexpressed with both LAB and TNBC (FIG. 10C). It is notable and worth reiterating that these biomarkers were identified as having differentially expressed levels in EVs and consistently and accurately differentiated between the breast cancer subtypes through their relative expression levels as defined herein. Furthermore, the present disclosure confirms that such expression levels can be measured from EVs isolated from biofluids and not only from tissue samples obtained through invasive biopsies.

Figure 11C:
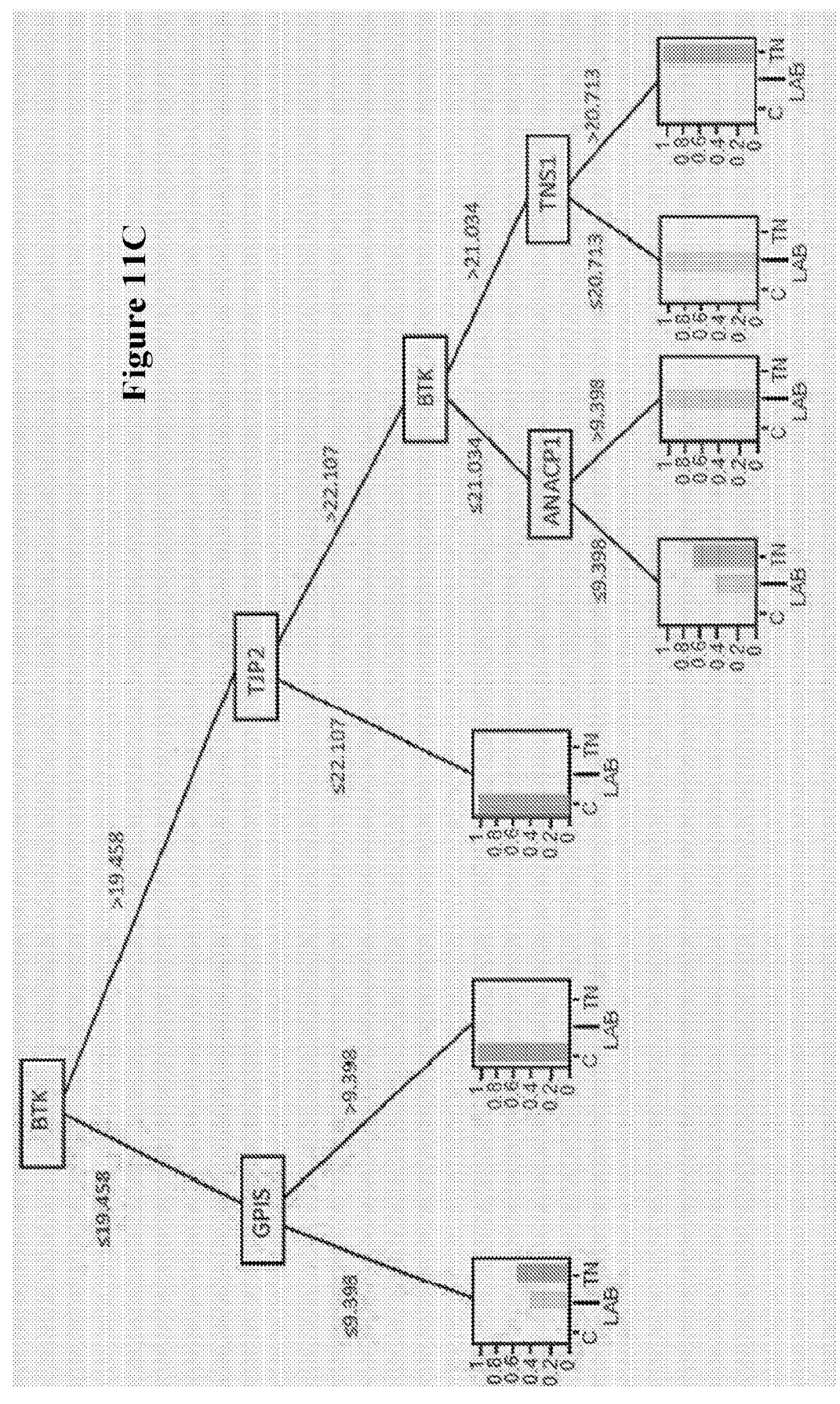

FIG. 11B illustrates the same data shown in FIG. 11A; namely, the percentage expression of BTK being below or equal to about 19.395 is indicative of a control or no breast cancer diagnosis; a percentage expression of BTK being above about 19.395 is indicative of breast cancer and, when taken in conjunction with the expression percentage of CCDCl6.1, indicates which subtype of breast cancer is present (i.e. BTK expression greater than about 21.439% indicates TNBC subtype; BTK expression between about 19.395-21.439%+CCDCl6.1 expression less than or equal to about 22.088% indicates TNBC subtype). Similarly, expression of BTK in the range of about 19.4-21.4 and expression of CCDCl6.1 at intensities of between about 22-23.5 was indicative of LAB (see FIG. 11B: BTK expression between about 19.395-21.439%+CCDCl6.1 expression less than about 22.088% indicates LAB subtype). FIGS. 11B and 11C illustrate the decision tree logic utilized to arrive at the diagnostic panels when the identified biomarkers are used in concert with each other in diagnostic expression profiles (as seen in FIGS. 9B and 11A).

FIG. 11C similarly shows a subtype diagnostic decision tree illustrating the findings discussed herein and several identified expression profiles. As illustrated in FIG. 11C, phosphorylated BTK with an intensity below about 19.5 and phosphorylated GPIS with an intensity above about 9.4 is indicative of no breast cancer (Control group), whereas phosphorylated BTK with an intensity below about 19.5 and phosphorylated GPIS with an intensity of below about 9.4 is indicative of either TN (60%) or LAB (40%). Likewise, phosphorylated BTK with an intensity between about 19.5 and about 21.0 and phosphorylated TJP2 with an intensity below about 22.1 is indicative of no breast cancer (Control), whereas phosphorylated BTK with an intensity between about 19.5-21.0 and phosphorylated ANACP1 with an intensity above about 9.4 is indicative of LAB. Additional diagnostic expression profiles are also provided in FIG. 11C.

In sum, the present disclosure provides more than 10,000 newly identified phosphoproteins, 900 acetoproteins, and 1,000 glycopeptides in plasma EVs through data-dependent acquisition. Of those, 135 phosphopeptides, 47 acetopeptides, and 98 glycopeptides were prioritized for quantification in individual plasma EV samples using scheduled PRM, through which a panel was successfully generated that comprises specific PTM sites that differentiate between breast cancer subtypes and, ultimately, aid in treatment assignment. Among the PTMs, phosphorylation appeared to be the most efficient at differentiating breast cancer subtypes; however, several effective glycosites and acetylated sites were also identified.

Figure 12:
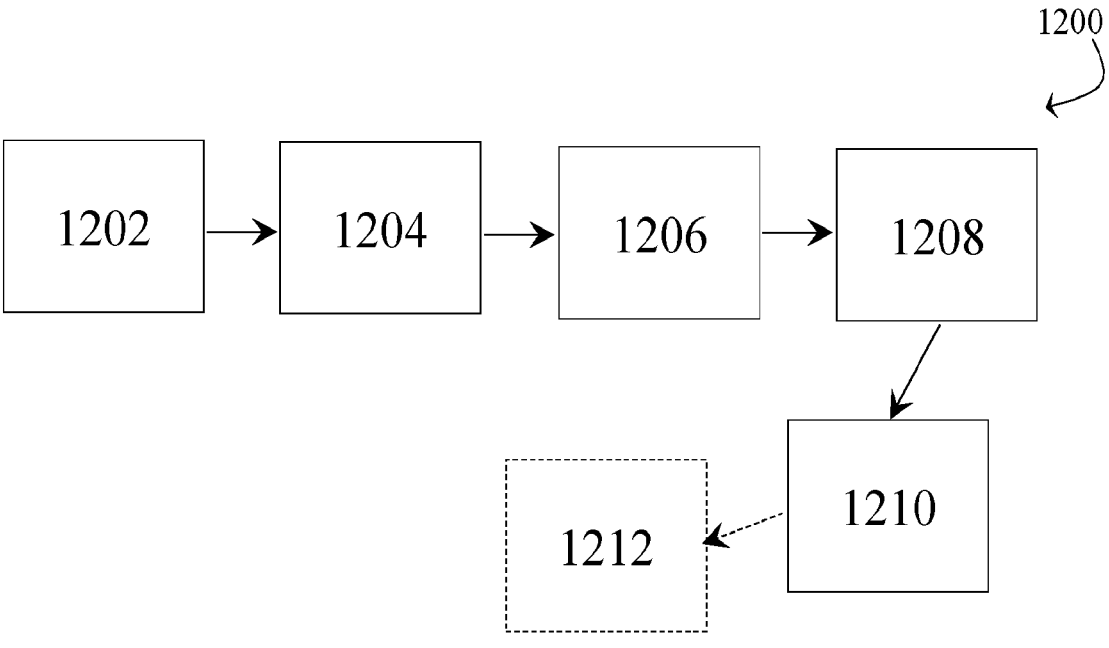
FIG. 12 is a flow chart representative of a method for determining breast cancer subtype in a subject using the methodologies and biomarkers described herein.

In view of the above findings, methods are provided for determining breast cancer subtype in a subject by analyzing specific PTMs and their concentrations present within EVs. Now referring to FIG. 12, a flow chart of at least one embodiment of one such method 1200 is shown.

Step 1202 comprises obtaining or having obtained an amount of a sample taken from a subject. In at least one exemplary embodiment, the subject comprises a human woman diagnosed with, or being screened for, breast cancer. As EVs are universally present in all biofluids, such sample may comprise any biofluid such as blood, urine, sweat, cerebrospinal fluid, bile, etc. Accordingly, where the sample is peripheral blood, a clinician need only withdraw a sample from the subject using standard techniques. Alternatively, where the sample is urine, a urine sample may be collected using known protocols. Notably, these collection methods are much less invasive and costly than the current standard of imaging techniques and biopsies and, importantly, are sufficiently sensitive that it is not necessary to wait for the disease to progress prior to achieving measurable levels.

At step 1204, a population of EVs are isolated from the sample pursuant to methods described herein and/or protocols known in the art. From the isolated EVs, one or more proteins or peptides are quantified, and any differential expression thereof is identified at step 1206 (differential as compared to a baseline which may be an established control value). This quantification/detection step 1206 may be performed using various modalities including, without limitation, performing mass spectrometry (LS-MS/MS or otherwise), a peptide assay, an enzyme linked immunosorbent assay (ELISA), employing an antibody against each of the one or more biomarkers in the panel, and/or employing an aptamer against each of the one or more biomarkers in the panel. Combinations of the foregoing quantification methods may also be employed.

At step 1208 any differential expression in the EV proteins or EV peptides is compared with a panel of biomarkers. The panel of biomarkers may be, for example, one or more phosphoproteins, glycoproteins, acetylated proteins, methylated proteins, and ubiquitinated proteins that are differentially expressed in cancer cells and, in a preferred embodiment, in different subtypes of breast cancer. In at least one embodiment, the panel of biomarkers comprises one or more of the proteins or genes (or fragments thereof) listed in Table 3, or any peptides or fragments thereof associated therewith.

In addition to a list of one or more biomarkers themselves, the panel of biomarkers may additionally identify particular patterns of expression of such biomarkers. As illustrated herein, certain combinations of over- and/or under-expression of these biomarkers as compared to a control are indicative of certain subtypes of breast cancer.

For example, and without limitation, the panel of biomarkers may comprise one or more expression patterns within the biomarkers that are indicative of a particular breast cancer subtype. In at least one embodiment such a pattern of expression may comprise overexpression of BTK and relatively equivalent expression of MYH9 (both as compared to a control) is indicative of the subject experiencing the TNBC subtype of cancer. Additionally or alternatively, an expression pattern indicating the subject is experiencing the LAB subtype of cancer may comprise overexpression of BTK and underexpression of MYH9 (both as compared to a control).

It will be appreciated that an exact match need not occur for there to be a positive correlation between an expression pattern and the differential expression in the EVs; rather, the positive correlation and/or match may be a 70% or greater correlation, 75%, 79%, 80%, 83%, 85%, or 88%, or more preferably, a 90%, 91%, 98%, or 99% correlation and still indicate a diagnosis of the associated condition/subtype.

At step 1210, the subject is diagnosed with the relevant subtype of breast cancer where the differential expression of the EVs positively correlates with at least one expression pattern of the biomarker panel. Perhaps more specifically, where an expression pattern of the biomarker panel is associated with the TNBC subtype, the subject's differential EV expression substantially matching or positively correlating with such expression pattern is indicative of the subject experiencing active TNBC. It will be appreciated that while the majority of the examples set forth herein address the TNBC and LAB subtypes, this method 1200 may also be employed with the HER2 and any other subtypes of breast cancer.

A diagnosis for a specific subtype of breast cancer can then drive treatment considerations. Accordingly, the method 1200 may optionally comprise step 1212, which comprises administration (or having administered) an appropriate treatment in view of the assigned diagnosis. In at least one embodiment, where the LAB subtype is diagnosed at step 1210, step 1212 comprises administering or having administered endocrine therapy to the subject. Alternatively, where HER2 is diagnosed, step 1212 may comprise administering or having administered a therapeutically effective dose of trastuzumab to the subject. Still further, if step 1210 indicates the breast cancer subtype is TNBC, step 1212 may comprise administering or having administered one or more of neoadjuvant chemotherapy, PARP inhibitors, and immunotherapy to the subject.

In an alternative embodiment of method 1200, method 1200 may be modified to monitor the treatment efficacy in a subject experiencing or having experienced breast cancer. Conventionally, once a patient is treated for breast cancer (whether it is a mastectomy, chemotherapy, and/or endocrine therapy, etc.), it is simply a wait-and-see situation; namely, the subject must wait and see if 1) the treatment was effective (i.e. removed all of the cancerous cells or is effectively reducing the size of a tumor); 2) if the cancer resurfaces either in the same location as before or in a secondary location in the body (following effective primary treatment); and 3) if recurrent breast cancer does occur, the identity of the subtype. The current standard is to monitor using visual imaging techniques, followed by a tissue biopsy, which necessarily means the cancer must have progressed to a state where visual tumors are present.

Unlike conventional techniques, the novel methods and biomarkers of the present disclosure provide the ability to almost immediately determine if a treatment is effective and/or successful, and to diagnose a recurrent breast cancer in a subject as soon as differential expression of PTMs are present within the subject's EVs, which happens concurrently with even initial cancer growth. Accordingly, in at least one embodiment, method 1200 may be performed to monitor treatment efficacy in a subject experiencing, or having experienced breast cancer, with steps 1202-1208 remaining the same.

However, in this embodiment, at step 1210, instead of diagnosing the subject, the panel of biomarkers is used to evaluate a therapeutic effect of the first treatment on the subject. If, for example, at step 1204 a differential expression in the isolated EVs is identified and positively correlated/matched with one or more expression patterns within the panel of biomarkers when compared at step 1208, it will be understood that the first treatment was not effective and an alternative therapy should be considered. Indeed, as with previous embodiments of method 1200, a positive correlation or match between an expression pattern in the panel of biomarkers and the differential expression of the EVs is indicative of the subject experiencing an active breast cancer. As such, at step 1210, the breast cancer subtype may also be determined, if desired, as previously described. In this manner, the present disclosure provides an easy, accurate, and noninvasive solution to monitor treatment efficacy, subtype breast cancer, and/or drive effective treatment decisions in breast cancer patients.

This technology can be used to generate simple and easy to use kits for determining a subtype of breast cancer in a subject. Indeed, the practical applications of the inventive biomarkers and methodologies set forth herein are vast and include not only identifying the breast cancer subtype in a patient, but also monitoring breast cancer treatment efficacy and quickly and accurately identifying recurrent breast cancer (and the subtype thereof). Significantly, in certain embodiments these kits may be configured for POC, unlike biopsies which must be sent away for analysis.

In at least one embodiment, a kit may comprise a means to detect and quantify a panel of biomarkers in EVs isolated from a biofluid sample. Such means for detection and quantification may comprise any of the modalities presented herein suitable for the same, as well as any now known or hereafter developed in the relevant art. For example, the means for detection and quantification may comprise antibodies or aptamers against the biomarkers of the panel. It will be appreciated that such antibodies and/or aptamers may be formulated pursuant to methods known in the art and it will be apparent to one of ordinary skill how to achieve the same.

The panel of biomarkers may be one or more phosphoproteins, glycoproteins, acetylated proteins, methylated proteins, and ubiquitinated proteins. Additionally, the panel of biomarkers may be as described in connection with method 1200; namely, including one or more of the markers listed in Table 3 or peptides or fragments thereof. Optionally, such kits may also comprise a means for collecting a biofluid sample such as a medical receptacle (e.g., a syringe, test tube, catheter, specimen cup, or the like). While various embodiments of compositions, systems, and methods hereof have been described in considerable detail, the embodiments are merely offered by way of non-limiting examples. Many variations and modifications of the embodiments described herein will be apparent to one of ordinary skill in the art in light of the disclosure. It will therefore be understood by those skilled in the art that various changes and modifications may be made, and equivalents may be substituted for elements thereof, without departing from the scope of the disclosure. Indeed, this disclosure is not intended to be exhaustive or too limiting. The scope of the disclosure is to be defined by the appended claims, and by their equivalents.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps disclosed herein should not be construed as limitations on the claims. In addition, the claims directed to a method and/or process should not be limited to the performance of their steps in the order written, and one skilled in the art can readily appreciate that the sequences may be varied and still remain within the spirit and scope of the present disclosure.

It is therefore intended that this description and the appended claims will encompass, all modifications and changes apparent to those of ordinary skill in the art based on this disclosure.

TABLE 2B

PRM Target Biomarkers. An "X" in the far-left column indicates the marker/site was subsequently validated with targeted proteomics and clinical validation methodologies.

| | PROTEIN NAME | GENE NAME |
|---|---|---|
| | Acetylation PRM Targets | |
| | Ig kappa chain V-II region FR;<br>Ig kappa chain V-II region RPMI 6410;<br>Ig kappa chain V-II region Cum | IGKV2D-28;<br>IGKV2D-26;<br>IGKV2D-30;<br>IGKV2-40;<br>IGKVA18;<br>IGKV2D-29 |
| | WD repeat-containing protein 1 | WDR1 |
| | Filamin-A; Filamin-B; Filamin-C | FLNA;<br>FLNB; FLNC |
| | ATP synthase subunit d, mitochondrial | ATP5H |
| X | Alpha-2-macroglobulin | A2M |
| X | Alpha-2-macroglobulin | A2M |
| X | Alpha-2-macroglobulin | A2M |
| | Apolipoprotein C-I; Truncated apolipoprotein C-I | APOC1 |
| | Fibrinogen alpha chain; Fibrinopeptide A;<br>Fibrinogen alpha chain | FGA |
| | Fibrinogen beta chain; Fibrinopeptide B;<br>Fibrinogen beta chain | FGB |
| | Fructose-bisphosphate aldolase A | ALDOA |
| | Fructose-bisphosphate aldolase A;<br>Fructose-bisphosphate aldolase C | ALDOA; ALDOC |
| | Fructose-bisphosphate aldolase A | ALDOA |
| | Glyceraldehyde-3-phosphate dehydrogenase | GAPDH |
| | Glyceraldehyde-3-phosphate dehydrogenase | GAPDH |
| | Alpha-enolase | ENO1 |
| | Acyl-CoA-binding protein | DBI |
| | Profilin-1 | PFN1 |
| | 60 kDa heat shock protein, mitochondrial | HSPD1 |
| | 60 kDa heat shock protein, mitochondrial | HSPD1 |
| | Vinculin | VCL |
| | Vinculin | VCL |
| | Filamin-A | FLNA |
| | 14-3-3 protein theta; 14-3-3 protein beta/alpha;<br>14-3-3 protein beta/alpha, N-terminally processed;<br>14-3-3 protein sigma; 14-3-3 protein zeta/delta | YWHAQ;<br>YWHAB;<br>SFN;<br>YWHAZ |
| | Myosin-9 | MYH9 |
| | Myosin-9; Myosin-10; Myosin-11; Myosin-14 | MYH9; MYH10;<br>MYH11; MYH14 |
| X | Myosin-9 | MYH9 |
| X | T-complex protein 1 subunit zeta | CCT6A |
| | Trifunctional enzyme subunit alpha,<br>mitochondrial; Long-chain enoyl-CoA<br>hydratase; Long chain 3-hydroxyacyl-CoA<br>dehydrogenase | HADHA |
| | Trifunctional enzyme subunit alpha,<br>mitochondrial; Long-chain enoyl-CoA<br>hydratase; Long chain 3-hydroxyacyl-CoA<br>dehydrogenase | HADHA |
| | Isocitrate dehydrogenase [NADP], mitochondrial | IDH2 |
| | Fatty acid synthase; [Acyl-carrier-protein]<br>S-acetyltransferase; [Acyl-carrier-protein]<br>S-malonyltransferase;<br>3-oxoacyl-[acyl-carrier-protein] synthase;<br>3-oxoacyl-[acyl-carrier-protein] reductase;<br>3-hydroxyacyl-[acyl-carrier-protein] dehydratase;<br>Enoyl-[acyl-carrier-protein] reductase;<br>Oleoyl-[acyl-carrier-protein] hydrolase | FASN |
| | T-complex protein 1 subunit gamma | CCT3 |
| | T-complex protein 1 subunit theta | CCT8 |

TABLE 2B-continued

PRM Target Biomarkers. An "X" in the far-left column indicates the marker/site was subsequently validated with targeted proteomics and clinical validation methodologies.

| PROTEIN NAME | GENE NAME |
|---|---|
| T-complex protein 1 subunit theta | CCT8 |
| Peroxisomal multifunctional enzyme type 2; | HSD17B4 |
| (3R)-hydroxyacyl-CoA dehydrogenase; | |
| Enoyl-CoA hydratase 2 | |
| Biliverdin reductase A | BLVRA |
| 10 kDa heat shock protein, mitochondrial | HSPE1 |
| Histone H4 | HIST1H4A |
| Ras-related protein Rab-1B; | RAB1B; |
| Putative Ras-related protein Rab-1C; | RAB1C; |
| Ras-related protein Rab-1A | RAB1A |
| Glutathione S-transferase omega-1 | GSTO1 |
| NAD(P) transhydrogenase, mitochondrial | NNT |
| Ras suppressor protein 1 | RSU1 |
| Centriole, cilia and spindle-associated protein | CCSAP |
| N-alpha-acetyltransferase 50 | NAA50 |
| Talin-1 | TLN1 |
| Talin-1 | TLN1 |
| Glycosylation PRM Targets | |
| Embigin | EMB |
| Alpha-1-antichymotrypsin; | SERPINA3 |
| Alpha-1-antichymotrypsin His-Pro-less | |
| Transforming growth factor beta-1; | TGFB1 |
| Latency-associated peptide | |
| Lymphocyte antigen 75 | LY75 |
| Integrin alpha-M | ITGAM |
| Integrin alpha-X | ITGAX |
| Alpha-1-antitrypsin; Short peptide from AAT | SERPINA1 |
| Tissue factor pathway inhibitor | TFPI |
| Tissue factor pathway inhibitor | TFPI |
| Probable G-protein coupled receptor 116 | GPR116 |
| Bone morphogenetic protein 6 | BMP6 |
| Receptor-type tyrosine-protein phosphatase eta | PTPRJ |
| Probable carboxypeptidase X1 | CPXM1 |
| Transmembrane protein 245 | TMEM245 |
| Pro-epidermal growth factor; | EGF |
| Epidermal growth factor | |
| Hypoxia up-regulated protein 1 | HYOU1 |
| Basal cell adhesion molecule | BCAM |
| CD109 antigen | CD109 |
| Fibrocystin-L | PKHD1L1 |
| Protocadherin Fat 1; Protocadherin Fat 1, | FAT1 |
| nuclear form | |
| Protein HEG homolog 1 | HEG1 |
| Neutrophil gelatinase-associated lipocalin | LCN2 |
| Receptor-type tyrosine-protein phosphatase eta | PTPRJ |
| Olfactomedin-4 | OLFM4 |
| Plexin-B2 | PLXNB2 |
| Plexin-B2 | PLXNB2 |
| Multimerin-1; Platelet glycoprotein Ia*; | MMRN1 |
| 155 kDa platelet multimerin | |
| Cholesteryl ester transfer protein | CETP |
| Integrin alpha-1 | ITGA1 |
| Lysosomal acid phosphatase | ACP2 |
| Lymphocyte antigen 75 | LY75 |
| Fibrocystin-L | PKHD1L1 |
| Semaphorin-7A | SEMA7A |
| Integrin alpha-5; Integrin alpha-5 heavy | ITGA5 |
| chain; Integrin alpha-5 light chain | |
| Disintegrin and metalloproteinase domain- | ADAM10 |
| containing protein 10 | |
| Anoctamin-6 | ANO6 |
| Integrin beta-1 | ITGB1 |
| Integrin beta-1 | ITGB1 |
| Integrin alpha-6; Integrin alpha-6 heavy | ITGA6 |
| chain; Integrin alpha-6 light chain; | |
| Processed integrin alpha-6 | |
| Multimerin-1; Platelet glycoprotein Ia*; | MMRN1 |
| 155 kDa platelet multimerin | |
| Leucine-rich alpha-2-glycoprotein | LRG1 |
| Multimerin-1; Platelet glycoprotein Ia*; | MMRN1 |
| 155 kDa platelet multimerin | |
| Multimerin-1; Platelet glycoprotein Ia*; | MMRN1 |
| 155 kDa platelet multimerin | |

TABLE 2B-continued

PRM Target Biomarkers. An "X" in the far-left column indicates the marker/site was subsequently validated with targeted proteomics and clinical validation methodologies.

| | PROTEIN NAME | GENE NAME |
|---|---|---|
| | Myosin regulatory light chain 12A; | MYL12A; |
| | Myosin regulatory light chain 12B; | MYL12B; |
| | Myosin regulatory light polypeptide 9 | MYL9 |
| | Integrin beta-2 | ITGB2 |
| | Olfactomedin-4 | OLFM4 |
| | Integrin alpha-X | ITGAX |
| | ERO1-like protein beta | ERO1LB |
| | Carcinoembryonic antigen-related cell adhesion | CEACAM8 |
| | molecule 8 | |
| | Fibroleukin | FGL2 |
| | Multimerin-1; Platelet glycoprotein Ia*; | MMRN1 |
| | 155 kDa platelet multimerin | |
| | Transmembrane 9 superfamily member 3 | TM9SF3 |
| | Transmembrane protein 206 | TMEM206 |
| | Disintegrin and metalloproteinase domain- | ADAM10 |
| | containing protein 10 | |
| | Multimerin-1; Platelet glycoprotein Ia*; | MMRN1 |
| | 155 kDa platelet multimerin | |
| | Lymphocyte antigen 75 | LY75 |
| X | Tyrosine-protein phosphatase non-receptor type | SIRPA |
| | substrate 1 | |
| | Follistatin-related protein 1 | FSTL1 |
| | Protein sel-1 homolog 1 | SEL1L |
| | Integrin alpha-5; Integrin alpha-5 heavy | ITGA5 |
| | chain; Integrin alpha-5 light chain | |
| | Major prion protein | PRNP |
| X | Apolipoprotein B-100; Apolipoprotein B-48 | APOB |
| X | Apolipoprotein B-100; Apolipoprotein B-48 | APOB |
| X | Apolipoprotein B-100; Apolipoprotein B-48 | APOB |
| | Protein O-glucosyltransferase 1 | POGLUT1 |
| | Lymphocyte cytosolic protein 2 | LCP2 |
| | Endothelin-converting enzyme 1 | ECE1 |
| | Kell blood group glycoprotein | KEL |
| | GTP-binding protein Rheb | RHEB |
| | GPI ethanolamine phosphate transferase 1 | PIGN |
| | Alpha-1-acid glycoprotein 1 | ORM1 |
| | Plexin-C1 | PLXNC1 |
| | Integrin alpha-M | ITGAM |
| | Sushi domain-containing protein 1 | SUSD1 |
| | Endoplasmin | HSP90B1 |
| | Cadherin-6 | CDH6 |
| | Cadherin-6 | CDH6 |
| | Protein sel-1 homolog 1 | SEL1L |
| | Cleft lip and palate transmembrane protein 1 | CLPTM1 |
| | Peptidyl-prolyl cis-trans isomerase B | PPIB |
| | Maltase-glucoamylase, | MGAM |
| | intestinal; Maltase; Glucoamylase | |
| | Prolow-density lipoprotein receptor-related | LRP1 |
| | protein 1; Low-density lipoprotein | |
| | receptor-related protein 1 85 kDa subunit; | |
| | Low-density lipoprotein receptor-related | |
| | protein 1 515 kDa subunit; Low-density | |
| | lipoprotein receptor-related | |
| | protein 1 intracellular domain | |
| | Metal transporter CNNM4 | CNNM4 |
| | Sortilin | SORT1 |
| | Afamin | AFM |
| | Neuroserpin | SERPINI1 |
| | P-selectin | SELP |
| | Integrin alpha-M | ITGAM |
| | Angiopoietin-1 | ANGPT1 |
| | Angiopoietin-related protein 6 | ANGPTL6 |
| | Chondroitin sulfate glucuronyltransferase | CHPF2 |
| | Protocadherin Fat 4 | FAT4 |
| | Corticosteroid-binding globulin | SERPINA6 |
| | Nicastrin | NCSTN |
| | Lysosome membrane protein 2 | SCARB2 |
| | Intercellular adhesion molecule 2 | ICAM2 |
| | Intercellular adhesion molecule 2 | ICAM2 |
| | Semaphorin-4D | SEMA4D |
| | Phosphorylation PRM Targets | |
| | PDZ and LIM domain protein 1 | PDLIM1 |
| | Kiev interaction trapped protein 1 | KRIT1 |

TABLE 2B-continued

PRM Target Biomarkers. An "X" in the far-left column
indicates the marker/site was subsequently validated with targeted
proteomics and clinical validation methodologies.

| | PROTEIN NAME | GENE NAME |
|---|---|---|
| | Apolipoprotein L1 | APOL1 |
| X | WAS/WASL-interacting protein family member 1 | WIPF1 |
| | Regulator of G-protein signaling 14 | RGS14 |
| | Eukaryotic translation initiation factor 5B | EIF5B |
| | Protein XRP2 | RP2 |
| | Serine/threonine-protein kinase 10 | STK10 |
| | Protein phosphatase 1 regulatory subunit 3D | PPP1R3D |
| X | MLN64 N-terminal domain homolog | STARD3NL |
| X | MLN64 N-terminal domain homolog | STARD3NL |
| | Band 3 anion transport protein | SLC4A1 |
| | Band 3 anion transport protein | SLC4A1 |
| | Band 3 anion transport protein | SLC4A1 |
| | Band 3 anion transport protein | SLC4A1 |
| | Band 3 anion transport protein | SLC4A1 |
| | Heat shock protein beta-1 | HSPB1 |
| | Integrin beta-1 | ITGB1 |
| | Protein kinase C beta type | PRKCB |
| | Glucose-6-phosphate isomerase | GPI |
| | Heat shock protein HSP 90-alpha | HSP90AA1 |
| | Tyrosine-protein kinase Lyn | LYN |
| | Clathrin light chain A | CLTA |
| | Protein 4.1 | EPB41 |
| X | Spectrin beta chain, erythrocytic | SPTB |
| | Coagulation factor V; | F5 |
| | Coagulation factor V heavy chain; Coagulation factor V light chain | |
| | Platelet glycoprotein Ib beta chain | GP1BB |
| | Platelet glycoprotein Ib beta chain | GP1BB |
| | cAMP-dependent protein kinase type II-alpha regulatory subunit | PRKAR2A |
| | Serine/threonine-protein kinase B-raf | BRAF |
| | Ankyrin-1 | ANK1 |
| | Ankyrin-1 | ANK1 |
| | Ankyrin-1 | ANK1 |
| | Ankyrin-1 | ANK1 |
| | Ankyrin-1 | ANK1 |
| X | Stathmin | STMN1 |
| X | Protein kinase C alpha type | PRKCA |
| | Vinculin | VCL |
| | Vinculin | VCL |
| | C5a anaphylatoxin chemotactic receptor 1 | C5AR1 |
| | Voltage-dependent anion-selective channel protein 1 | VDAC1 |
| | Eukaryotic translation initiation factor 4B | EIF4B |
| | Transgelin-2 | TAGLN2 |
| X | Rho GTPase-activating protein 25 | ARHGAP25 |
| | Epidermal growth factor receptor substrate 15 | EPS15 |
| | Phosphatidylserine synthase 1 | PTDSS1 |
| | Hsc70-interacting protein; Putative protein FAM10A4 | ST13; ST13P4 |
| | Hsc70-interacting protein; Putative protein FAM10A4 | ST13; ST13P4 |
| | Vasodilator-stimulated phosphoprotein | VASP |
| | Lipopolysaccharide-responsive and beige-like anchor protein | LRBA |
| X | Ras-related protein Rab-7a | RAB7A |
| | Coatomer subunit alpha; Xenin; Proxenin | COPA |
| | Coatomer subunit alpha; Xenin; Proxenin | COPA |
| | Pituitary tumor-transforming gene 1 protein-interacting protein | PTTG1IP |
| | Ras-related protein Rab-8A | RAB8A |
| | Microtubule-associated protein 1A; MAP1A heavy chain; MAP1 light chain LC2 | MAP1A |
| | Microtubule-associated protein 1A; MAP1A heavy chain; MAP1 light chain LC2 | MAP1A |
| | Disabled homolog 2 | DAB2 |
| | Spectrin beta chain, non-erythrocytic 1 | SPTBN1 |
| | Focal adhesion kinase 1 | PTK2 |
| X | Tyrosine-protein kinase BTK | BTK |
| X | Tyrosine-protein kinase BTK | BTK |
| | Dematin | DMTN |
| | Nexilin | NEXN |
| | Nexilin | NEXN |
| | Nexilin | NEXN |

TABLE 2B-continued

PRM Target Biomarkers. An "X" in the far-left column
indicates the marker/site was subsequently validated with targeted
proteomics and clinical validation methodologies.

| | PROTEIN NAME | GENE NAME |
|---|---|---|
| | Syntaxin-4 | STX4 |
| | 5-AMP-activated protein kinase catalytic subunit alpha-1 | PRKAA1 |
| | 26S proteasome non-ATPase regulatory subunit 2 | PSMD2 |
| | Growth factor receptor-bound protein 10 | GRB10 |
| | Sorting nexin-17 | SNX17 |
| | Protein phosphatase 1 regulatory subunit 7 | PPP1R7 |
| | Myosin light chain kinase, smooth muscle; Myosin light chain kinase, smooth muscle, deglutamylated form | MYLK |
| X | Zyxin | ZYX |
| X | Zyxin | ZYX |
| X | Zyxin | ZYX |
| X | Zyxin | ZYX |
| | Septin-7 | SEPTIN7 |
| X | Coiled-coil domain-containing protein 6 | CCDC6 |
| | Uncharacterized protein KIAA1109 | KIAA1109 |
| | TBC1 domain family member 10B | TBC1D10B |
| | Lymphocyte antigen 6 complex locus protein G6f | LY6G6F |
| | CapZ-interacting protein | RCSD1 |
| | Phostensin | PPP1R18 |
| | Aftiphilin | AFTPH |
| | Myosin phosphatase Rho-interacting protein | MPRIP |
| | Serine/threonine-protein kinase TAO1 | TAOK1 |
| | Nuclear fragile X mental retardation-interacting protein 2 | NUFIP2 |
| | SUZ domain-containing protein 1 | SZRD1 |
| | Phosphofurin acidic cluster sorting protein 2 | PACS2 |
| | Glucocorticoid-induced transcript 1 protein | GLCCI1 |
| X | Unconventional myosin-XVIIIb | MYO18B |
| | C-Maf-inducing protein | CMIP |
| | Hsc70-interacting protein; Putative protein FAM10A4 | ST13; ST13P4 |
| | Hsc70-interacting protein; Putative protein FAM10A4 | ST13; ST13P4 |
| | Pumilio homolog 2 | PUM2 |
| | Protein bicaudal D homolog 2 | BICD2 |
| | Partitioning defective 3 homolog | PARD3 |
| | Protein lifeguard 3 | TMBIM1 |
| | Protein phosphatase 1 regulatory subunit 14A | PPP1R14A |
| | Abscission/NoCut checkpoint regulator | ZFYVE19 |
| | Trafficking protein particle complex subunit 9 | TRAPPC9 |
| X | Msx2-interacting protein | SPEN |
| | GAS2-like protein 1 | GAS2L1 |
| X | DnaJ homolog subfamily C member 2; DnaJ homolog subfamily C member 2, N-terminally processed | DNAJC2 |
| X | Anaphase-promoting complex subunit 1 | ANAPC1 |
| | WD repeat-containing protein 13 | WDR13 |
| | STE20-like serine/threonine-protein kinase | SLK |
| | Uncharacterized protein C1orf198 | C1orf198 |
| | Golgi phosphoprotein 3 | GOLPH3 |
| | Protein phosphatase 1 regulatory subunit 3E | PPP1R3E |
| X | Protein Njmu-R1 | C17orf75 |
| X | Tensin-1 | TNS1 |
| | Cas scaffolding protein family member 4 | CASS4 |
| | NCK-interacting protein with SH3 domain | NCKIPSD |
| | E3 ubiquitin-protein ligase KCMF1 | KCMF1 |
| | LisH domain and HEAT repeat-containing protein KIAA1468 | KIAA1468 |
| | Epidermal growth factor receptor substrate 15-like 1 | EPS15L1 |
| | Epidermal growth factor receptor substrate 15-like 1 | EPS15L1 |
| X | Tight junction protein ZO-2 | TJP2 |
| X | Tight junction protein ZO-2 | TJP2 |
| | LIM domain and actin-binding protein 1 | LIMA1 |
| | Rab5 GDP/GTP exchange factor | RABGEF1 |
| | Arf-GAP with SH3 domain, ANK repeat and PH domain-containing protein 1 | ASAP1 |
| | Conserved oligomeric Golgi complex subunit 5 | COG5 |
| | Microtubule-actin cross-linking factor 1, isoforms 1/2/3/5 | MACF1 |
| | Ubiquitin carboxyl-terminal hydrolase 24 | USP24 |

TABLE 2B-continued

PRM Target Biomarkers. An "X" in the far-left column
indicates the marker/site was subsequently validated with targeted
proteomics and clinical validation methodologies.

| | PROTEIN NAME | GENE NAME |
|---|---|---|
| | Endoribonuclease Dicer | DICER1 |
| X | Phospholipid-transporting ATPase IA | ATP8A1 |
| | Rab GTPase-activating protein 1 | RABGAP1 |
| X | TSC22 domain family protein 4 | TSC22D4 |
| | Talin-1 | TLN1 |
| | Insulin receptor substrate 2 | IRS2 |
| | G-protein-signaling modulator 3 | GPSM3 |
| | FH1/FH2 domain-containing protein 1 | FHOD1 |

The invention claimed is:

1. A method of determining breast cancer subtype in a subject comprising:

obtaining or having obtained an amount of a sample taken from a subject;

isolating a population of extracellular vehicles (EVs) in the sample;

identifying differential expression of one or more proteins or peptides in the isolated EVs as compared to an expression level of such EV proteins or EV peptides in a control;

comparing the differential expression in the isolated EVs to one or more expression profiles within a panel of biomarkers, wherein each expression profile in the panel is associated with a subtype of breast cancer;

diagnosing the subject with the triple negative breast cancer (TNBC) subtype of breast cancer when the differential expression in the isolated EVs positively correlates with a first expression profile of the panel of biomarkers, the first expression profile comprising overexpression of phosphorylated bruton tyrosine kinase (BTK) and equivalent expression of acetylated myosin heavy chain 9 (MYH9), both as compared to a control; or diagnosing the subject with the luminal A/B breast cancer (LAB) subtype of breast cancer when the differential expression in the isolated EVs positively correlates with a second expression profile of the panel of biomarkers, the second expression profile of the panel of biomarkers comprising overexpression of BTK and underexpression of MYH9, both as compared to a control; and administering, to the subject, a therapeutically effective dose of:

an endocrine therapy comprising an aromatase inhibitor or an antiestrogen, when the subject is diagnosed with the LAB subtype of breast cancer;

one or more of neoadjuvant chemotherapy, PARP inhibitors, and immunotherapy, when the subject is diagnosed with the TNBC subtype of breast cancer;

or trastuzumab, when the differential expression correlates to a third expression profile associated with a third subtype of breast cancer comprising the HER2 subtype of breast cancer.

2. The method of claim 1, wherein the panel of biomarkers further comprises one or more of the proteins or genes selected from the following: tight junction protein 2 (TJP2), coiled-coil domain containing 6 (CCDC6.1), zyxin, (ZYX), ankyrin repeat and pH domain 1 (ASAP1), Ras-related protein Rab-7a (RAB7A), myosin 18B (MYO18B), rho GTPase activating protein 25 (ARHGAP25), STARD3 N-terminal like or mentho (STARD3NL), spectrin beta, non-erythrocytic 1 (SPTBN1), TSC22 domain family member 4 (TSC22D4), spen family transcriptional repressor (SPEN), DNAJ heat shock protein family (Hsp40) member C2 (DNAJC2), phospholipid-transporting ATPase IA (TP8A1), protein kinase C alpha (PRKCA), anaphase promoting complex subunit 1 (ANAPC1), stathmin 1 (STMN1), chromosome 17 open reading frame 75 (C17orf75), ATPase phospholipid transporting 8A1 (ATP8A1), tensin 1 (TNS1), WAS/WASL interacting protein family member 1 (WIPF1), chaperonin containing TCP1 subunit 6A (CCT6A), alpha-2-macroglobulin (A2M), apolipoprotein B (APOB), signal regulatory protein alpha (SIRPA) or peptide or a fragment thereof.

3. The method of claim 1, wherein the step of identifying differential expression further comprises quantifying a level of expression of one or more proteins or peptides in the isolated EVs.

4. The method of claim 1, wherein the sample comprises blood, plasma, urine or serum from a human subject.

5. The method of claim 3, wherein the step of identifying is performed using mass spectrometry, a peptide assay, an enzyme linked immunosorbent assay (ELISA), an antibody against each of the one or more proteins or peptides, or an aptamer against each of the one or more proteins or peptides.

6. The method of claim 1, wherein the comparing step further comprises performing parallel reaction monitoring or multi-reaction monitoring between the isolated EVs and the panel of biomarkers and scoring a degree of correlation between the same.

7. The method of claim 1, wherein after the subject has received a first treatment for the diagnosed subtype of breast cancer the method further comprises;

isolating a population of extracellular vehicles (EVs) in the sample;

identifying a differential expression of one or more proteins or peptides in the isolated EVs as compared to an expression level of such EV proteins or EV peptides in a control;

comparing the differential expression in the isolated EVs to the one or more expression profiles within the panel of biomarkers to evaluate a therapeutic effect of the first treatment on the subject.

8. The method of claim 7, wherein the first treatment comprises one or more of a chemotherapy, an endocrine therapy, and a mastectomy.

9. The method of claim 7, further comprising administering or having administered a second treatment where a result of the panel evaluation is indicative of the subject experiencing a recurrent breast cancer.

10. The method of claim 9, further comprising using the panel of biomarkers to identify a subtype of the recurrent breast cancer in the subject by diagnosing the subject with the subtype of breast cancer associated with the at least one expression profile of the panel with which the differential expression in the isolated EVs positively correlates.

* * * * *